US012670696B2

(12) United States Patent
Mansoor et al.

(10) Patent No.: US 12,670,696 B2
(45) Date of Patent: Jun. 30, 2026

(54) METHODS AND SYSTEMS FOR CLASSIFYING A MEDICAL IMAGE DATASET

(71) Applicant: Siemens Healthcare GmbH, Erlangen (DE)

(72) Inventors: Awais Mansoor, Potomac, MD (US); Ingo Schmuecking, Yardley, PA (US); Rikhiya Ghosh, Livingston, NJ (US); Oladimeji Farri, Upper Saddle River, NJ (US); Jianing Wang, Plainsboro, NJ (US); Bogdan Georgescu, Princeton, NJ (US); Sasa Grbic, Plainsboro, NJ (US); Philipp Hoelzer, Tokyo (JP); Dorin Comaniciu, Princeton, NJ (US)

(73) Assignee: SIEMENS HEALTHINEERS AG, Forchheim (DE)

( * ) Notice: Subject to any disclaimer, the term of this patent is extended or adjusted under 35 U.S.C. 154(b) by 274 days.

(21) Appl. No.: 18/519,389

(22) Filed: Nov. 27, 2023

(65) Prior Publication Data

US 2024/0177454 A1  May 30, 2024

Related U.S. Application Data

(60) Provisional application No. 63/385,255, filed on Nov. 29, 2022.

(30) Foreign Application Priority Data

Mar. 29, 2023   (EP) .................................... 23165181

(51) Int. Cl.
*G06V 10/764* (2022.01)
*G06T 7/00* (2017.01)
(Continued)

(52) U.S. Cl.
CPC .......... *G06V 10/764* (2022.01); *G06T 7/0012* (2013.01); *G16H 15/00* (2018.01); *G16H 30/20* (2018.01); *G06T 2207/30168* (2013.01)

(58) Field of Classification Search
CPC .... G06V 10/764; G06V 10/82; G06V 10/774; G06T 7/0012; G06T 2207/30168;
(Continued)

(56) References Cited

U.S. PATENT DOCUMENTS 7,822,274 B2   10/2010  Sinop et al.
9,760,807 B2    9/2017  Zhou et al.
(Continued)

FOREIGN PATENT DOCUMENTS

EP          3828818 A1    6/2021
EP          4227960 A1    8/2023
WO   WO 2023274599 A1    1/2023

OTHER PUBLICATIONS

Digital Imaging and Communications in Medicine (DICOM); Part 1: "Introduction and Overview"; Version PS3.1 2018c; 2018; from https://www.dicomstandard.org/current////////DICOM PS3.1 2020c standard (or any later or earlier version of said standard) (p. 4 of priority version=202202370)////////.
(Continued)

*Primary Examiner* — Siamak Harandi
(74) *Attorney, Agent, or Firm* — Harness, Dickey & Pierce, P.L.C.

(57) ABSTRACT

Provided are computer-implemented methods and systems for classifying a medical image data set. In particular, a method is provided comprising the steps of receiving the medical image dataset of a patient, of providing a first classification stage configured to classify the medical image dataset as normal or not-normal, of providing a second classification stage different than the second classification
(Continued)

stage and configured to classify the medical image dataset as normal or not-normal, and of subjecting the medical image dataset to the first classification stage to classify the medical image dataset as normal or not-normal. Further, the method comprises subjecting the medical image dataset to the second classification stage to classify the medical image dataset as normal or not-normal, if the medical image dataset is classified as normal in the first classification stage.

19 Claims, 6 Drawing Sheets

(51) Int. Cl.
  *G16H 15/00* (2018.01)
  *G16H 30/20* (2018.01)
(58) Field of Classification Search
  CPC ........ G16H 15/00; G16H 30/20; G16H 50/70;
                                                          G16H 50/20
  See application file for complete search history.

(56) References Cited

U.S. PATENT DOCUMENTS

| | | |
|---|---|---|
| 11,393,229 B2 | 7/2022 | Zhou et al. |
| 2009/0067693 A1 | 3/2009 | Shinagawa |
| 2009/0092300 A1 | 4/2009 | Jerebko et al. |
| 2016/0321427 A1 | 11/2016 | Bogoni et al. |
| 2020/0286615 A1* | 9/2020 | Hartung ................. G16H 15/00 |
| 2023/0071400 A1* | 3/2023 | Abdolell ................ G16H 30/40 |
| 2024/0005493 A1 | 1/2024 | Yerebakan et al. |

OTHER PUBLICATIONS

Kattoju et al; Utility of Chest X-ray in Health Checkup Program in Detecting Pleuroparenchymal Lesion in a Tertiary Care Hospital; 2021 Journal of Association of Pulmonologist of Tamil Nadu | Published by Wolters Kluwer.

Vaswani A. et al.:"Attention Is All You Need", arXiv:1706.03762v5 [cs.CL] Dec. 6, 2017; 2017.

Keski-Filppula et al; Using artificial intelligence to detect chest X-rays with no significant findings in a primary health care setting in Oulu, Finland; https://doi.org/10.48550/arXiv.2205.08123; arXiv:2205.08123; Cornell University; 2022.

Nabulsi et al; Deep learning for distinguishing normal versus abnormal chest radiographs and generalization to two unseen diseases tuberculosis and COVID-19; nature portfolio; Scientific Reports; 2021) 11:15523; | https://doi.org/10.1038/s41598-021-93967-2.

Dyer et al; Diagnosis of normal chest radiographs using an autonomous deep-learning algorithm; Clinical Radiology 76 (2021) 473. e9e473.e15; https://doi.org/10.1016/j.crad.2021.01.015; 2021.

Lopez-Gonzalez Rafael et al; "Automated Chest Radiographs Triage Reading by a Deep Learning Referee Network Quantitative Imaging Biomarkers in Medicine"; MEDRXIV; Jan. 6, 2021; pp. 1-9; XP055891011; DOI: 10.1101/2021.06.01.21257399; 2021.

Rajaraman S et al; "Assessment of an ensemble of machine learning models toward abnormality detection in chest radiographs"; 2019 41st Annual International Conference of the IEEE Engineering in Medicine and Biology Society (EMBC); IEEE; Jul. 31, 2019; pp. 3689-3692; XP033624629; DOI: 10.1109/EMBC. 2019.8856715; 2019.

* cited by examiner

FIG 1

METHODS AND SYSTEMS FOR CLASSIFYING A MEDICAL IMAGE DATASET

CROSS-REFERENCE TO RELATED APPLICATION (S)

The present application claims priority under 35 U.S.C. § 119 to European Patent Application No. 23165181.1, filed Mar. 29, 2023, and U.S. Provisional Application No. 63/385, 255, filed Nov. 29, 2022, the entire contents of each of which are incorporated herein by reference.

FIELD

One or more example embodiments of the invention concern the field of medical image data processing. For example, embodiments of the invention concern the processing of medical image data for classifying the medical image data. For example, embodiments of the invention concern the classification of medical image data for providing a medical diagnosis.

RELATED ART

The volume of medical images that need to be processed keeps growing from year to year, which creates an ever-increasing burden on the radiologists tasked with analyzing and interpreting these images. Further, due to conventional medical practices, some types of medical images, such as chest x-rays or chest CT images (e.g., for lung cancer screening), have a high rate of "normals" (i.e., cases without any radiographically visible abnormality). Reviewing normals can take up a substantial amount of radiologists' time, which could be better spent reviewing and analyzing medical images that actually have radiographically visible abnormalities. Therefore, if there were a mechanism to pre-filter normals (especially for types of medical images that tend to have high rates of normals), it could help free radiologists' time to review and analyze abnormal cases that require more detailed interpretation for the purposes of making treatment decisions, providing differential diagnoses, or assessing disease prognoses.

SUMMARY

One or more example embodiments of the present invention provide methods and systems configured to efficiently classify medical image data in order to reduce the workload of the user. In particular, one or more example embodiments of the present invention provide systems and methods configured to securely identify normal medical image datasets which do require less attention from the user as compared to medical image datasets showing abnormalities.

This object is, in particular, solved by a method for classifying a medical image dataset, a corresponding system, a corresponding computer-program product, and a computer-readable storage medium according to the independent claims and aspects as herein described. Alternative and/or preferred embodiments are object of the dependent claims and the further aspects and examples as herein described.

BRIEF DESCRIPTION OF THE DRAWINGS

Characteristics, features and advantages, as well as the manner they are achieved, become clearer and more understandable in the light of the following description of embodiments, which will be described in detail with respect to the figures. This following description does not limit the invention on the contained embodiments. Same components, parts or steps can be labeled with the same reference signs in different figures. In general, the figures are not drawn to scale. In the following:

FIG. 1 schematically depicts an embodiment of a system for classifying a medical image dataset according to an embodiment;

DETAILED DESCRIPTION

Figure 2:
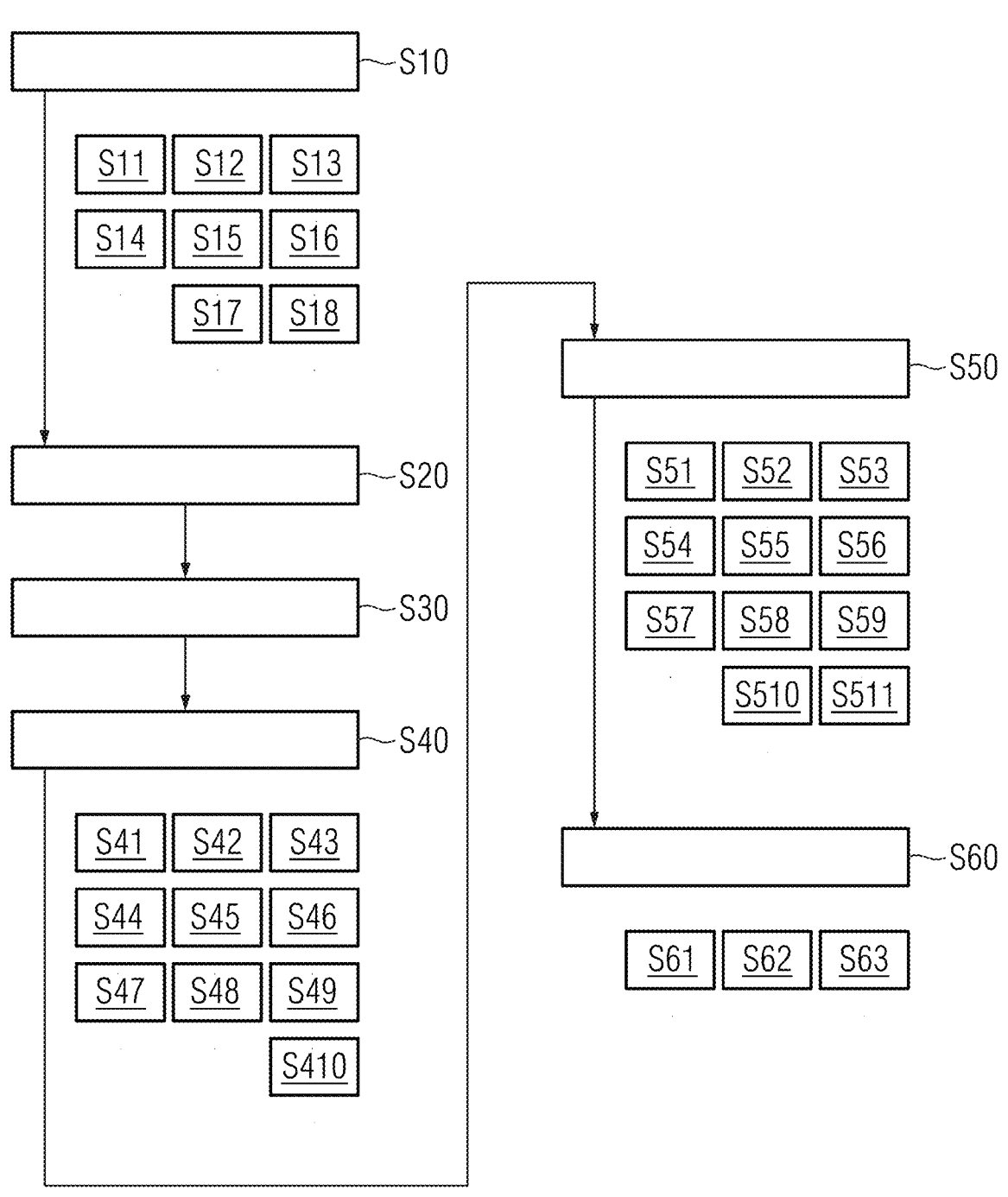
FIG. 2 schematically depicts a method for classifying a medical image dataset according to an embodiment.

Some radiology practices use technicians to pre-sort abnormal and normal candidate images manually. However, this is still a time-consuming process and technicians' work generally must still be reviewed by a radiologist before a final determination can be made that no abnormality is present.

Further, some machine learning algorithms have been developed to assist in pre-screening medical images for radiologists. However, these algorithms likewise have issues. In particular, most machine learning algorithms have been developed to address only one type of findings (e.g. pulmonary nodules). Therefore, a radiologist still needs to review each medical image for what are commonly known as "incidental findings," which may be clinically relevant and must be reported. For example, a machine learning algorithm configured to identify normal chest exams still has to be aware of any sort of abnormality (e.g., associated with any of the mediastinum, lung fields, heart, ribs, spine, or abdomen). To date, however, most algorithms show <100% performance in negative predictive value and do not address all of the "incidental findings" that a radiologist would be required to identify. Accordingly, current machine learning algorithms leave some doubt as to whether they can reliably determine that there are no clinically relevant findings within a medical image.

As previously noted, some machine learning algorithms have been developed to assist in pre-screening medical images. However, the medical practice must still perform a quality control step by the radiologist to overread at least a proportion of the normals to monitor the performance of the software and manage the risk of false negatives. Therefore, although these machine learning algorithms could generally be helpful, they do not solve the inherent issues of occupying radiologists' time and broad applicability to a wide range of types of medical images and conditions.

In the following, technical solutions according to the present invention are described with respect to the claimed systems as well as with respect to the claimed methods. Features, advantages, or alternative embodiments described herein can likewise be assigned to other claimed objects and vice versa. In other words, claims addressing the inventive method can be improved by features described or claimed with respect to the systems. In this case, e.g., functional features of the methods are embodied by objective units or elements of the systems.

The technical solutions will be described both with regard to methods and systems for providing information and also with regard to methods and systems for providing trained functions. Features and alternate forms of embodiments of data structures and/or functions for methods and systems for providing can be transferred to analogous data structures and/or functions for methods and systems for providing trained functions. Analogous data structures can, in particular, be identified by using the prefix "training". Furthermore, the trained functions used in methods and system for providing information can, in particular, have been adjusted and/or trained and/or provided by methods and systems for adjustment of trained functions.

According to an aspect, a computer-implemented method for classifying a medical image dataset is provided. The method comprises a plurality of steps. A step is directed to receive (or obtain) the medical image dataset showing a body part of a patient. A further step is directed to providing a first classification stage configured to classify the medical image dataset as normal or not-normal. A further step is directed to provide a second classification stage different than the first classification stage configured to classify the medical image dataset as normal or not-normal. A further step is directed to subject the medical image dataset to the first classification stage so as to classify the medical image dataset as normal or not-normal. A further step is directed to subjecting the medical image dataset to the second classification stage so as to classify the medical image dataset as normal or not-normal if the medical image dataset is classified as normal in the first classification stage.

According to an aspect, a computer-implemented method for classifying a medical image dataset is provided. The method comprises a plurality of steps. A step is directed to receive (or obtain) the medical image dataset showing a body part of a patient. A further step is directed to providing a first classification stage configured to classify the medical image dataset as normal or not-normal. A further step is directed to provide a second classification stage different than the first classification stage configured to classify the medical image dataset as normal or not-normal. A further step is directed to subject the medical image dataset to the first classification stage so as to classify the medical image dataset as normal or not-normal. A further step is directed to subjecting the medical image dataset to the second classification stage so as to classify the medical image dataset as normal or not-normal. A further step is directed to classify the medical image dataset as normal if the medical image dataset is classified as normal in the first and second classification stages and as not-normal otherwise.

The medical image dataset may relate to a medical image study. The medical image dataset may relate to three-dimensional datasets providing three dimensions in space or two dimensions in space and one dimension in time, to two-dimensional datasets providing two dimensions in space, and/or to four-dimensional datasets providing three dimensions in space and one dimension in time.

The medical image dataset may depict a body part of a patient in the sense that it contains three-dimensional image data of the patient's body part. The medical image dataset may be representative of an image volume. The patient's body part may be comprised in the image volume.

The medical image dataset comprises image data, for example, in the form of a two- or three-dimensional array of pixels or voxels. Such arrays of pixels or voxels may be representative of intensity, absorption or other parameters as a function of three-dimensional position, and may, for example, be obtained by suitable processing of measurement signals obtained by a medical imaging modality.

A medical imaging modality corresponds to a system used to generate or produce medical image data. For example, a medical imaging modality may be a computed tomography system (CT system), a magnetic resonance system (MR system), an angiography (or C-arm X-ray) system, a positron-emission tomography system (PET system), an ultrasound imaging system or the like. Specifically, computed tomography is a widely used imaging method and makes use of "hard" X-rays produced and detected by a specially rotating instrument. The resulting attenuation data (also referred to as raw data) is presented by a computed analytic software producing detailed images of the internal structure of the patient's body parts. The produced sets of images are called CT-scans which may constitute multiple series of sequential images to present the internal anatomical structures in cross sections perpendicular to the axis of the human body. Magnetic Resonance Imaging (MRI), to provide another example, is an advanced medical imaging technique which makes use of the effect magnetic field impacts on movements of protons. In MRI machines, the detectors are antennas and the signals are analyzed by a computer creating detailed images of the internal structures in any section of the human body.

Accordingly, the depicted body part of the patient in general will comprise a plurality of anatomies and/or organs (also denoted as compartments or anatomic structures). Taking a chest image as an example, the medical image dataset may show lung tissue, bones, e.g. the rib cage, heart and aorta, lymph nodes and others.

The medical image dataset may comprise a plurality of images or image slices. The slices may respectively show a cross-sectional view of the image volume. The slices may comprise a two-dimensional array of pixels or voxels as image data. The arrangement of slices in the medical image dataset may be determined by the imaging modality or by any post-processing scheme used. Further, slices may artificially be defined in the imaging volume spanned by the medical image dataset. Optionally, this may happen as a function of the image data comprised in the medical image dataset in order to optimally pre-process the medical image dataset for the ensuing diagnostic workflow.

The medical image dataset may be stored in a standard image format such as the Digital Imaging and Communications in Medicine (DICOM) format and in a memory or computer storage system such as a Picture Archiving and Communication System (PACS), a Radiology Information System (RIS), a Vendor Neutral Archive (VNA), an Electronic Health Record (HER) storage or database, and the like. Whenever DICOM is mentioned herein, it shall be understood that this refers to the "Digital Imaging and Communications in Medicine" (DICOM) standard, for example according to the DICOM PS3.1 2020c standard (or any later or earlier version of said standard).

"Receiving" or "Obtaining" may mean that the medical image dataset is directly received/obtained from the medical imaging modalities. Further, "receiving" or "obtaining" may mean that the medical image dataset is retrieved from an appropriate memory such as a picture archiving and communication system (PACS) or any other suitable medical image storing facility or database.

According to some examples, the first and/or second classification stage are independent from one another. This may mean that the second classification stage may process the medical image dataset independently from any classification result of the first classification stage (and vice versa) so as to provide a classification result.

According to some examples, the first and/or second classification stage may comprise a plurality of sub-steps of classifying the medical image dataset, the results of which may be aggregated to classify the medical image dataset as normal or not-normal in the respective classification stage.

According to some examples, the first and/or second classification stage may be configured to separately classify individual slices of the medical image dataset, the results of which may be aggregated to classify the medical image dataset as normal or not-normal in the respective classification stage.

Further, according to some examples, the first and/or second classification stages may comprise applying one or more image processing steps or image pre-processing steps to the medical image dataset comprising but not limited to image segmentation, image enhancement, and/or image correlation steps.

According to some examples, the first and/or second classification stage may respectively comprise applying one or more classification algorithms to the medical image dataset. The one or more classification algorithms may be configured to provide a classification result indicating if the medical image dataset (or parts of it) is normal or not-normal. In the first and/or second classification stages, individual classification results of a plurality of classification algorithms may be aggregated to classify the medical image dataset as normal or not-normal in the respective classification stage.

According to some examples, the first and second classification stage are different in the sense that they respectively employ a different way of and/or use different means for classifying the medical image dataset as normal or not-normal. According to some examples, the first and second classification stage are different in the sense that the respective classification results and/or ways and/or means complement one another. According to some examples, the first and second classification stages may differ in the number and type of (pre-) processing steps and/or classification algorithms applied. In particular, first and second classification stages may respectively use different classification algorithms (i.e., may be configured to apply different classification algorithms in the first classification stage than in the second classification stage).

According to some examples, subjecting the medical image dataset to one of the first and second classification stages may mean applying the respective classification stage to the medical image dataset. According to some examples, subjecting the medical image dataset to one of the first and second classification stages may mean inputting the medical image dataset in the respective classification stage.

According to some examples, "normal" may mean that the medical image dataset is medically inconspicuous. According to some examples, "normal" may mean that the medical image dataset does not comprise (or indicate) any medical findings. According to some examples, "normal" may mean that the medical image dataset does not comprise (or indicate) any medical abnormalities.

According to some examples, the term "normal" may also apply for the different parts (i.e., compartments, organs, or anatomic structures, slices) shown in the medical image dataset. Accordingly, "normal" may mean that a compartment shown or slice comprised in the medical image dataset is medically inconspicuous. According to some examples, "normal" may mean that a compartment shown or slice comprised in the medical image dataset does not comprise (or indicate) any medical findings (or medical abnormalities).

A medical finding may indicate a certain condition or pathology of the patient which is relevant for the diagnosis of the patient and which requires the attention of a user. A medical finding may be an anatomical structure that differentiates the patient from other patients. A medical finding may be a medical abnormality. A medical finding may be located within different organs of the patient (e.g., within the lung of a patient, or within the liver of a patient) or in between the organs of the patient. In particular, a medical finding may be a foreign body. In particular, a medical finding may be a neoplasm (also denoted as "tumor"), in particular, a benign neoplasm, an in situ neoplasm, a malignant neoplasms and/or a neoplasms of uncertain/unknown behavior. In particular, a medical finding can be a nodule, in particular, a lung nodule. In particular, a medical finding may be a lesion, in particular, a lung lesion.

According to some examples, the classification result provided in the first and/or second classification stage indicates whether or not the medical image dataset, as a whole, is normal. According to some examples, parts of the medical image dataset may be normal while other parts of the medical image dataset are not normal. According to some examples, the medical image dataset would then be classified as not-normal and only classified as normal if all parts are classified as normal.

According to some examples, "normal" may mean that the medical image dataset does not comprise (or indicate) any actionable medical abnormalities. Such non-actionable medical abnormalities may not require any immediate action from the user. Examples for non-actionable abnormalities could be, e.g., anatomical variants, degenerative changes, e.g. bone changes in elderly patients, healed fractions, or tiny lung nodules which do not require follow-up. Other examples for such non-actionable findings which could still classify the medical image dataset as normal are "hardware" which has been imaged such as surgical clips, (neck) laces, implants, ECG leads, etc. According to some examples, alternative wording for normal as used herein may be non-actionable and/or an alternative wording for not-normal as used herein may be actionable.

According to some examples, not-normal relates to anything which cannot be classified as normal. Accordingly, not-normal may comprise medical image data (the entire set or parts thereof) where medical findings or abnormalities are actively recognized. Accordingly, not-normal may comprise medical image data (the entire set or parts thereof) where actionable medical findings or abnormalities are actively recognized. Further, not-normal may comprise medical image data (the entire set or parts thereof) which could not be affirmed as being normal and/or where a confidence of the classification result "normal" is too low, e.g., below a predetermined threshold.

In other words, embodiments of the invention propose to use a two-stage classification scheme to filter those medical image datasets which are normal. With that, normal and not-normal medical image datasets can reliably be classified. In turn, this enables a user to focus on those medical image datasets which are not-normal. This reduces the workload for the user. Moreover, due to the two-stage classification, it can be made sure that subtle findings are not overlooked which are of particular concern for the user.

According to some examples, the classification result of a medical image dataset being normal or not-normal may be conceived as providing a medical diagnosis. Since, according to some examples, the first and second classification stages comprise processing the medical image dataset, a method is provided which is configured to provide a medical diagnosis by an automated processing of physiological measurements (in the form of the medical image dataset).

According to an aspect, the first classification stage comprises inputting the medical image dataset in a first trained classifier configured to recognize if the medical image dataset is normal, and the second classification stage comprises inputting the medical image dataset in a second trained classifier different than the first trained classifier and configured to recognize medical abnormalities in medical image datasets.

According to some examples, the first and/or second trained classifier comprises one or more machine-learned functions. In general, a machine-learned function mimics cognitive functions that humans associate with other human minds. In particular, by training based on training data, the machine-learned function is able to adapt to new circumstances and to detect and extrapolate patterns. Other terms for machine-learned function, may be trained function, trained machine learning model, trained mapping specification, mapping specification with trained parameters, function with trained parameters, algorithm based on artificial intelligence, or machine learned algorithm.

In general, parameters of a machine-learned function can be adapted via training. In particular, supervised training, semi-supervised training, unsupervised training, reinforcement learning and/or active learning can be used. Furthermore, representation learning can be used. In particular, the parameters of the machine-learned function can be adapted iteratively by several steps of training. In the presented case, codes of the medical ontology could be attributed to sample queries by an expert. This annotated data can then be used as a ground truth to train the machine-learning function.

In particular, a machine-learned function can comprise a neural network, a support vector machine, a decision tree and/or a Bayesian network, and/or the trained function can be based on k-means clustering, Q-learning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

In particular, the trained classifier configured to recognize if the medical image dataset is normal may have been trained to detect image data which does not give rise to medical findings.

According to some examples, the method may comprise providing the first and/or second trained classifiers which may comprise holding the classifier (s) available in a suitable storage accessible by the computing unit executing the method. Further, providing the classifier (s) may comprise downloading it by said computing unit.

According to some examples, the second trained classifier may be a (medical) abnormality detection algorithm. Thus, the second classification stage may be configured to classify the medical image dataset as not-normal, if the second trained classifier detects an abnormality.

Abnormality detection algorithms may generally be configured to detect medical findings or abnormalities in medical image data. In principle, a plethora of functionalities and methods is known for such computer aided detection and classification of abnormalities—all of which may be implemented in the abnormality detection algorithm. For instance, reference is made to US 2009/0 092 300 A1, US 2009/0 067 693 A1, or US 2016/0 321 427 A1, the contents of which are incorporated herein in their entirety by reference.

According to some examples, the abnormality detection algorithm (and, thus, the second trained classifier) may be configured such that their level of sensitivity (and, in turn, their specificity) can be adjusted. According to some examples, the sensitivity and the specificity of the abnormality detection algorithm may be adjusted with its point of operation.

The usage of the two classification stages, one being configured to recognize if the medical image data is normal and one being configured to actively recognize abnormalities, has the advantage that the problem of identifying normal medical image datasets can be approached from two angles. With that, a more secure classification of normal medical image datasets can be facilitated. Thereby, the optional usage of machine-learned functions in general has the advantage that a more comprehensive and faster screening of the medical image datasets can be made. In this regard, machine-learned functions may identify patterns and attributes in the available data that are not accessible for a human. In particular, with the active recognition of abnormalities, it can be made sure that also subtle findings are not overlooked because of the dedicated usage of a classification stage configured to detect abnormalities.

According to an aspect, the second trained classifier has been trained to recognize medical abnormalities based on training medical image datasets which were annotated as containing one or more medical abnormalities.

According to an aspect, the first trained classifier has been trained to recognize normal image data based on training medical image datasets which were annotated as not containing any medical abnormalities.

According to an aspect, the second classification stage comprises inputting the medical image dataset in a first trained classifier configured to recognize if the medical image dataset is normal. The first classification stage, according to some examples, may then comprise image pre-processing steps, like segmentations or an assessment of the image quality as herein described.

According to an aspect, the method further comprises providing an output indicating a classification result of the medical image dataset being normal or not-normal, wherein the output comprises am indication of any recognized medical abnormality.

With that, the user not only gets an overall classification result but also indication where the medical problems of the medical image dataset may lie. This improves the workflow and reduces the workload for the user.

According to an aspect, the first and/or second classification stage comprise segmenting at least one compartment from the medical image dataset to define a segmented dataset, and the first and/or second classification stage are configured to classify the image data of the segmented dataset as normal or not-normal, wherein the medical image dataset is classified as normal if the image data of the segmented dataset is classified as normal, and the medical image dataset is classified as not-normal otherwise.

A compartment may generally relate to an entity of the patient's organism which may be qualified as normal or not-normal. For instance, a compartment may relate to an organ, an organ part, an organ function, an anatomic structure, an anatomy, a functional unit of the patient's organism and so forth.

According to some examples, segmenting a compartment may comprise identifying the compartment in the image data of the medical image dataset and/or delineating the compartment in the medical image dataset. According to some examples, the step of segmenting may provide the image data from the medical image dataset which pertains to the segmented compartment.

Generally, as mentioned, any depicted body part will comprise a plurality of compartments such as, taking a chest image as an example, lung lobes, the bone compartment (e.g., comprising the rib structure or the spine), the heart, hardware such as implants, pacemakers, or catheters, and so forth. According to some examples, the step of segmenting may comprise segmenting a plurality of (different) compartments so as to provide image data respectively pertaining to the segmented compartments.

In principle, a plethora of functionalities and methods is known for image segmentation in medicine—all of which may be implemented in the segmentation steps as herein described. For instance, reference is made to U.S. Pat. No. 7,822,274 B2, U.S. Pat. No. 9,760,807 B2, U.S. Pat. No. 11,393,229 B2 the contents of which are incorporated herein in their entirety by reference.

According to some examples, the segmented dataset comprises the image data of one or more of the segmented compartments, preferably, in a way that the image data of any of the segmented compartments can be provided separately. To this end, the segmented dataset may provide a data layer for each segmented compartment comprising the image data of the respective compartment.

Alternatively, the segmented data may also comprise the image data of only one segmented compartment. Thus, there may be a separate segmented dataset for each segmented compartment specifically comprising the image data of that compartment.

In many cases not all of these anatomies are relevant for a given diagnosis and, what is more, not all anatomies are handled equally well by available image processing algorithms. The segmentation in this context allows to identify anatomies and organs in the image data and delineate them against neighboring structures, background and unstructured tissue. This makes it possible to apply dedicated image analysis procedures that have been optimized for the specific organ.

According to an example, the first and/or second classification stage comprises inputting the segmented dataset in a first trained classifier configured to recognize if the at least one compartment is normal, and the first and/or the second classification stage comprises inputting the medical image dataset in a second trained classifier different than the first trained classifier and configured to recognize medical abnormalities in image data pertaining to the at least one compartment.

By segmenting the medical image dataset, the classification can be rendered more specific as, for instance, dedicated trained classifiers may be used. With that, the detection of normal medical image datasets can be rendered more accurate and the workload of the user can be reliably reduced.

According to an aspect, the first and/or second classification stage comprise segmenting a plurality of different compartments from the medical image dataset to define segmented image data for each of the segmented compartments (or a segmented dataset comprising segmented image data for each of the segmented compartments, or a segmented dataset for each of the segmented compartments respectively comprising segmented image data of the segmented compartment), and the first and/or second classification stage are configured to classify the segmented image data (of the segmented dataset (s)) as normal or not-normal, wherein the medical image dataset is classified as normal if the segmented image data of each of the segmented compartments is classified as normal, and the medical image dataset is classified as not-normal otherwise.

By taking multiple compartments into account which all have to be "normal" for the medical image dataset to be classified as normal on the whole, the identification of normal medical image datasets can be rendered more accurate. This reliably reduces the workload of a user having to review medical image datasets as she or he may focus on the not-normal ones.

According to an aspect, the method further comprises providing an output indicating a classification result of the medical image dataset being normal or not-normal, wherein the output comprises an indication of the classification result for each of the plurality of compartments.

In doing so, the user gets an indication which of the compartments are normal even though the medical image dataset as whole came out as not-normal. With that, a user may focus on those compartments which are not-normal and the workflow is rendered more efficient.

According to an aspect, the first and/or second classification stage comprise segmenting at least one compartment from the medical image dataset to define a segmented dataset, and the first and/or second classification stage are configured to independently classify i) the image data of the (optionally: entire) medical image dataset as normal or not-normal and ii) the image data of the segmented dataset as normal or not-normal, wherein the medical image dataset is classified as normal if the medical image data of medical image dataset is classified as normal and the image data of the segmented dataset is classified as normal, and the medical image dataset is classified as not-normal otherwise.

In other words, a classification on a level of the entire medical image dataset and a classification on a level of the at least one compartment are performed. Only if both are normal, the overall classification can be normal. This improves the accuracy and reliability of the method.

According to an aspect, the first classification stage and/or the second classification stage comprise: providing a plurality of different trained classifiers each configured to specially classify image data of a specific compartment as normal or not-normal, selecting at least one trained classifier from the plurality of different trained classifiers according to the at least one compartment, and classifying the image data of the segmented dataset as normal or not-normal using the at least one selected trained classifier.

By providing trained classifiers which specifically been trained to classify a given compartment, the identification of normal medical image datasets can be rendered more accurate.

According to an aspect, the first and/or second classification stage comprise obtaining a prior medical image dataset, the prior medical image dataset showing the body part of the patient at a different point in time than the medical image dataset. Further, the first and/or second classification stage are configured to classify the medical image dataset as normal or not-normal additionally based on the prior medical image dataset and, in particular, based on determining a change between the medical image dataset and the prior medical image dataset.

"Change" may, in particular, relate to clinically relevant variations in the image data from the prior medical image dataset to the medical image dataset. To quantify such changes, first and/or second classification stages may be configured to generate a registration of the prior medical image dataset and the medical image dataset and determine the change based on the registration. Further details and examples how changes in image data can be quantified can, for instance, be inferred from EP 3 828 818 A1, the contents of which are incorporated herein in their entirety.

According to other examples, such changes may be quantified based on a semantic image understanding of the medical image dataset and the prior medical image dataset on the basis of which semantic image understanding elements of both medical image datasets may be related to one another. For instance, the semantic image understanding may be configured to recognize compartments in medical image datasets. Further details and examples, for instance, be inferred from EP 22182378.4, the contents of which are incorporated herein in their entirety.

The consideration of prior images may serve as a reference for classifying the current medical image dataset. For instance, changes of the image data may be detected which might give insights into clinically relevant alternations which should be notified to the user as not-normal. Further, taking prior images into account has the advantage that prior abnormalities can be taken into account for classifying the current medical image dataset. All in all, this leads to a more secure differentiation of normal images from not-normal images.

According to some examples, the prior medical image dataset was acquired with a medical imaging modality different than the medical imaging modality the medical image dataset was acquired with. For instance, while the medical image dataset was acquired with a computed tomography imaging modality, the prior medical image dataset could have been acquired with a magnetic resonance imaging modality or a positron-emission tomography imaging modality. According to other examples, the medical image dataset could have been acquired with a chest X-Ray scan using an X-Ray modality while the prior medical image dataset was acquired with a computed tomography imaging modality. This brings about the advantage that different kinds of image data may be considered for determining if the medical image dataset is normal.

According to some examples, the first and/or second classification stage may comprise selecting the prior medical image dataset from a plurality of candidate prior medical image datasets of the patient based on a comparability (or: by quantifying a comparability) of the respective candidate prior medical image dataset with the medical image dataset.

According to some examples, the comparability may be determined based on an anatomical overlap of the imaged regions of the medical image dataset and the candidate prior medical image dataset. For further details, reference is made to WO 2023/274 599 A1, the contents of which are incorporated herein in their entirety by reference.

According to some examples, the first and/or second classification stages comprise segmenting at least one compartment from the medical image dataset to define a segmented dataset and segmenting the at least one compartment from the prior medical image dataset to define a segmented prior dataset. Further, the first and/or second classification stage are configured to classify the medical image dataset as normal or not-normal additionally based on the segmented dataset and the segmented prior dataset and, in particular, based on determining a change between the segmented dataset and the segmented prior dataset.

According to some examples, classifying the medical image dataset based on the prior medical image dataset may comprise obtaining one or more prior findings from the prior medical image dataset and classifying the medical image dataset based on the one or more prior findings.

According to some examples, classifying the medical image dataset based on the one or more prior findings may comprise any one of: adjusting a sensitivity for classifying the medical image dataset as not-normal in the first and/or second classification stage, selecting one or more trained classifiers based in the one or more prior findings, adjusting a sensitivity of the one or more selected trained classifiers, segmenting at least one compartment from the medical image dataset to define a segmented dataset based on the one or more prior findings, and/or determining a change of the one or more prior findings based on the medical image dataset.

According to some examples, obtaining the prior findings may comprise applying an abnormality detection algorithm configured to detect medical findings in medical image datasets to the prior medical image dataset. Thereby, according to some examples, the abnormality detection algorithm may be configured as elsewhere herein described.

According to an aspect, the first and/or second classification stage comprise obtaining a plurality of prior medical image datasets, the prior medical image datasets showing the body part of the patient respectively at a different point in time than the medical image dataset. Further, the first and/or second classification stage are configured to classify the medical image dataset as normal or not-normal additionally based on the prior medical image datasets and, in particular, based on determining a change between the medical image dataset and the prior medical image datasets, and/or in particular, based on determining a trend of a change between the medical image dataset and the prior medical image datasets.

With that, a trending over a plurality of prior medical image datasets may be achieved, which is helpful for more securely determining if a finding is normal or not-normal (or actionable or non-actionable).

According to an aspect, the first and/or second classification stage comprise obtaining at least one image quality parameter for the medical image dataset, and the first and/or second classification stage are configured to classify the medical image dataset as not-normal based on the at least one image quality parameter.

Taking the image quality into account may help to filter for medical image datasets where an automatic classification into normal or not-normal is not readily possible and/or potentially flawed with uncertainty. Accordingly, the classification provided can be rendered more accurate.

According to some examples, the at least one image quality parameter may comprise any one of: a signal-to-noise-ratio of the medical image dataset, a contrast of the medical image dataset, a field of view depicted by the medical image dataset, an image resolution of the medical image dataset, or an imaging parameter used upon acquiring the medical image dataset.

By computing, for instance, the signal-to-noise-ratio of the medical image dataset, it can be determined if the medical image dataset has a sufficient quality for the ensuing automated classification. The same holds true for the contrast or the image resolution. By evaluating the field of view or imaging parameters it can be determined of the body part of the patient is completely or sufficiently imaged.

According to some examples, classifying based on the at least one image quality parameter may comprise classifying the medical image dataset as normal if the image quality parameter indicates a sufficient image quality and classifying the medical image dataset as not-normal otherwise.

According to some examples, classifying based on the at least one image quality parameter may comprise comparing the at least one image quality parameter to a predetermined threshold and classifying the medical image dataset as normal or not-normal based on the comparison.

According to some examples, the method further comprises obtaining supplementary data associated with the medical image dataset, the supplementary data optionally comprising demographic data of the patient, environmental data, lab data, a reason for the acquisition of the medical image dataset ("reason for the exam)", a diagnostic task to be performed for the patient, and/or a medical report of the patient, wherein the first and/or second classification stage are configured to classify the medical image dataset additionally based on the supplementary data.

According to some examples, the supplementary data may be supplementary non-image data.

According to some examples, the demographic data may comprise the age, gender, pre-existing illnesses or conditions, care settings of the patient (e.g., inpatient vs. outpatient vs. intensive care). According to some examples, environmental data may relate to a geographic location of the patient (e.g., some geographic populations have high prevalence of calcified granulomas, while others may have a disposition for lung cancer), an environmental pollution or other environmental conditions the patient is subjected to such as allergens, temperature, climate, etc.—all of which may influence the disposition of the patient for a certain disease and, thus, may affect the classification (or classification sensitivity) into normal or not-normal (or actionable or not-actionable).

According to some examples, lab data may comprise laboratory test results of the patient such as blood values. According to some examples, the medical report may comprise a prior (procedural) report of the patient.

By taking supplementary data into account, the classification can be rendered more accurate and more reliable. With that, the support for the user can be improved. For instance, it can be determined what the medical image dataset is supposed to show based on the demographic data or the diagnostic task or the medical report. Further, it can be assessed if the supplementary data indicates any prior findings which require a specific treatment of the medical image dataset in the classification.

In this regard, environmental data may relate to circumstances such as temperature, allergic conditions, etc. which affect the wellbeing of the patient and, thus, may influence the ensuing classification.

In particular, the supplementary data may comprise natural language text which may be structured or unstructured.

According to some examples, classifying the medical image dataset based on the supplementary data, may comprise obtaining one or more prior findings from the supplementary data, in particular, comprising a medical report, and classifying the medical image dataset based on the one or more prior findings.

According to some examples, classifying the medical image dataset based on the one or more prior findings may comprise any one of: adjusting a sensitivity for classifying the medical image dataset as not-normal in the first and/or second classification stage, selecting one or more trained classifiers based in the one or more prior findings, adjusting a sensitivity of the one or more selected trained classifiers, segmenting at least one compartment from the medical image dataset to define a segmented dataset based on the one or more prior findings, and/or determining a change of the one or more prior findings based on the medical image dataset.

According to some examples, obtaining one or more prior findings may comprise providing a natural language processing algorithm configured to identify medical findings in natural language text and inputting the supplementary data in the natural language processing algorithm so as to identify the one or more prior findings.

The natural language processing algorithm may be configured to recognize and/or understand natural language and, in particular, individual items such as words in input containing natural language. The natural language processing algorithm may be based on a trained or machine-learned function. As an alternative, the natural language processing algorithm may be rule-based. Providing the natural language algorithm may comprise holding the algorithm available in a suitable storage accessible by the computing unit executing the method. Further, providing the algorithm may comprise downloading it by said computing unit.

According to some examples, the natural language processing algorithm comprises a transformer network. According to some examples, the trained function comprises a transformer network.

A transformer network is a neural network architecture generally comprising an encoder, a decoder or both an encoder and decoder. In some instances, the encoders and/or decoders are composed of several corresponding encoding layers and decoding layers, respectively. Within each encoding and decoding layer preferably there is an attention mechanism. The attention mechanism, sometimes denoted as self-attention, is able to relate data items such as words in the query to other data items within the query. The self-attention mechanism for instance allows the model to examine a word within the query and determine the relative importance of other words within the query for the word being examined. Further, the transformer network may comprise a classification module configured to map the output of the encoder or decoder to a set of learned outputs, which are the codes of the medical ontology in the present case.

Training of a transformer model according to some examples may happen in two stages, a pretraining and a finetuning stage. In the pretraining stage, a transformer model may be trained on a large corpus of data to learn the underlying semantics of the problem. Such pretrained transformer models are available for different languages. For certain applications described herein, the fine-tuning may comprise further training the transformer network with medical texts with expert annotated meanings and/or medical ontologies such as RadLex and/or SNOMED.

An advantage of transformer networks is that, due to the attention mechanism, transformer networks can efficiently deal with long-range dependencies in input data. Further, encoders used in transformer networks are capable of processing data in parallel which saves computing resources in inference.

For a review on transformer networks, reference is made to Vaswani et al., "Attention Is All You Need", in arXiv: 1706.03762, Jun. 12, 2017, the contents of which are herein included by reference in their entirety. Further details and examples how changes in image data can be quantified can, for instance, be inferred from EP 23156314.9, the contents of which are incorporated herein in their entirety.

According to some examples, the method further comprises adjusting a sensitivity of the first and/or second classification stage based on the supplementary data.

In particular, adjusting the sensitivity may comprise adjusting a sensitivity of the first and/or second trained classifier. Further, in particular, this may comprise adjusting a sensitivity of the abnormality detection algorithm.

The term "sensitivity" (alternative expressions are "level of sensitivity" or "sensitivity level") as used herein may pertain to the sensitivity with which image data is identified as not-normal and thus requires expert review. In general, the higher the level of sensitivity is, the higher is the likelihood that a certain feature present in the medical image dataset is identified. Thereby, the level of sensitivity may pertain to a decision threshold above which image data is qualified as not-normal. In general, higher levels of sensitivity may produce more not-normal medical image datasets. Hence, higher levels of sensitivity will allow to capture more (and ideally all) medical image datasets which are actually not normal but will also lead to more false positives, i.e., otherwise normal images which will be flagged as not-normal. In other words, a higher level of sensitivity may entail a reduced level of specificity. According to some examples, the sensitivity may be adjusted by adjusting the operating point or point of operation of the respective classification stage or any classification algorithm therein comprised.

While it may not be desired to have high levels of sensitivities across the board (as this will lead to an increased number of normals being classified as not-normal), this may be desirable if there are indications that the medical image dataset is not-normal As such indications may be present in the supplementary data, basing the adjustment of the sensitivity on the supplementary data has the advantage that a targeted adjustment may be made.

If for instance, a prior report indicates that a patient suffers from a certain disease, the sensitivity of a corresponding classifier may be increased. The same holds true if the demographic data indicates that the patient has a certain risk for a particular disease or if the diagnostic task already contains a suspected diagnosis.

According to some examples, adjusting a sensitivity based on the supplementary data may comprise determining an indication for the medical image dataset being not-normal based on the supplementary data and increasing the sensitivity based on the indication. According to some examples, determining an indication may comprise providing a natural language processing algorithm configured to identify an indication for the medical image dataset being not-normal in the supplementary data and, in particular, in natural language text, and inputting the supplementary data in the natural language processing algorithm so as to determine the indication.

According to an aspect, the first classification stage and/or the second classification stage comprise: providing a plurality of different trained classifiers each configured to specially classify image data as normal or not-normal, selecting at least one trained classifier from the plurality of different trained classifiers based on the supplementary data, and classifying the medical image dataset as normal or not-normal using the at least one selected trained classifier.

With that, dedicated classifiers may be selected based on the circumstances of the case. For instance, if the supplementary data indicates a predisposition of the patient for a certain disease, a trained classifiers specifically configured to detect the certain disease may be selected.

According to an aspect, the method further comprises checking if one or more compartments of relevance can be established based on the supplementary data, segmenting one or more actual compartments from the medical image dataset, checking if the one or more compartments of relevance are comprised in the actual compartments, and classifying the medical image dataset as not-normal if the no anatomical structures of relevance can be established and/or classifying the medical image dataset as not-normal if at least one compartment of relevance is not comprised in the actual compartments.

The compartment (s) of relevance can be conceived as a region of interest which can be ascertained based on the supplementary data. If, for instance, a diagnostic task relates to the lung of a patient, the medical image dataset should show the lung of the patient to allow for a completion of the diagnostic task. If not, there might be a problem regarding the medical image dataset which requires the review of the user. Thus, it can be advantageous to classify the image dataset as not-normal. Similarly, it can be advantageous if the user is notified if no region of interest can be inferred in the first place since it is unclear to what task needs to be done. With that, the method can be rendered more fail-safe and provides more support for the user.

According to an aspect, the first and/or second classification stage comprise calculating a confidence value for a classification result of classifying the medical image dataset as normal or not-normal, and classifying the medical image dataset as not-normal if the confidence value is below a predetermined threshold.

According to some examples, the confidence value quantifies how confident a certain classification is. Thus, the classification result is automatically brought back as not-normal if it is too uncertain. In other words, in cases of doubt, the medical image dataset is classified as not-normal raising the bar for a normal classification. Accordingly, the normal class is rendered more reliable which may improve the safety of the approach in routine reading.

According to an aspect, the method comprises modifying a worklist of a user based on a classification result of classifying the medical image dataset as normal or not-normal, the worklist comprising a task for a user associated with the medical image dataset.

According to some examples, the worklist may, besides the task, comprise a plurality of further different tasks associated with the medical image dataset or different datasets. The worklist may be provided to a user in an electronic form, e.g., via a user interface.

With that, the result of the processing is transferred into a result the user can immediately use. Thereby, the worklist prioritization is a particularly efficient interface to the user assisting her or him to fulfill the task of providing medical diagnoses.

According to an aspect, modifying the worklist comprises: prioritizing the task associated with the medical image dataset in the worklist if the medical image dataset is classified as not-normal and/or as comprising abnormalities, and/or de-prioritizing the task associated with the medical image dataset in the worklist or removing the task associated with the medical image dataset from the worklist if the medical image dataset is classified as normal, and/or affirming a state of the task associated with the medical image dataset in the worklist if the confidence value is below the predetermined threshold, and/or partitioning the worklist into a normal and not-normal section and placing the task associated with the medical image dataset in the normal or not-normal part based on the classification result.

With the above modifications, the worklist can be effectively restructured based on the classification result. This improves the accessibility of the results for the user.

According to an aspect, the method further comprises generating a medical report based on a classification result of classifying the medical image dataset as normal or not-normal, and providing the medical report.

According to some examples, providing the medical report comprises forwarding the medical report to the user.

By automatically generating a medical report, the user is not only provided with a work product which readily fits into the clinical routine, but which intrinsically reflects the classification result. Accordingly, the method is rendered more efficient as the workload of the user is reduced.

According to an aspect, the step of generating comprises pre-filling the medical report based on the classification result of the first and/or second classification stage, and/or the prior medical image dataset (if any), and/or the supplementary data (if any), and/or the one or more prior findings (if any), and/or the change between the medical image dataset and the prior medical image dataset (if any).

According to an aspect, generating the medical report comprises selecting a report template from a plurality of candidate report templates based on the classification result, and auto-filling the report template based on the classification result and/or any intermediate result of the first and/or second classification stage, and/or the prior medical image dataset (if any), and/or the supplementary information (if any), and/or the one or more prior findings (if any), and/or the change between the medical image dataset and the prior medical image dataset (if any).

According to some examples, generating the medical report comprises determining if one or more of the one or more prior findings have resolved based on the classification result, if so, explicitly indicate this in the medical report, and, optionally, not indicate normal classification results in the medical report otherwise.

This makes allowance for the fact that inconspicuous parts often need not to be explicitly addressed in medical reports unless 'normal' constitutes an improvement of a previous state.

According to an aspect, the step of providing comprises forwarding the medical report to a user depending on the classification result and/or archiving the medical report without forwarding to the user depending on the classification result. According to some examples, the step of providing comprises forwarding the medical report to the user if the classification result of the medical image dataset is not-normal and not forwarding the medical report to the user otherwise.

With that, a user may see the medical report based on the classification result and, thus, dependent on the priority of the case. In particular, the user is not bothered with standard reports where everything is normal. Accordingly, the method may be rendered more efficient and the workload of the user may be further reduced.

According to an aspect, the method further comprises receiving feedback regarding a classification result of classifying the medical image dataset as normal or not-normal, and adjusting the first and/or second classification stage and/or the trained classifiers based on the feedback.

According to some examples, the feedback may comprise (re-)classifying the medical image dataset as normal by the user. According to some examples, adjusting the first and/or second classification stage and/or the trained classifiers may be carried out in discrete updates at predetermined periods of time or by way of continuous updates (using continuously adaptive algorithms).

By adapting the first and/or second classification stage and/or the trained classifiers based on feedback from the user, the algorithms involved can be continuously improved. This improves the accuracy and reliability of the method.

According to an aspect, the method further comprises providing or outputting a classification result of classifying the medical image dataset as normal or not-normal (based on classifying the medical image dataset as normal or not-normal by the first and/or second classification stage). According to an aspect, outputting may comprise providing the classification result to a user.

According to an aspect, the method comprises determining a medical diagnosis based on a classification result of classifying the medical image dataset as normal or not-normal (based on classifying the medical image dataset as normal or not-normal by the first and/or second classification stage) and providing the medical diagnosis. According to some examples, the medical diagnosis comprises an indication whether or not the medical image dataset is normal.

According to an aspect, the method comprises providing an indication (or: explanation) as to why a classification result of classifying the medical image dataset as normal or not-normal is normal and/or not-normal. In particular, providing an indication may comprise providing an indication of a compartment (e.g., of the at least one compartment) which was classified as not-normal and/or an indication of any abnormality or medical finding detected in the medical image dataset.

According to an aspect a method for providing a quality measure of a medical database is provided, wherein the database comprises a plurality of classified medical image datasets each having a classification status of being classified into normal and not-normal, in particular, by users of the database. The method comprises applying the method of classifying medical image datasets according to one or more aspects and/or examples as herein described to the plurality of classified medical image datasets, so as to generate, for each of the plurality of classified medical image datasets a classification result of the respective classified medical image dataset being normal or not-normal, determining a quality measure based on the classification results and the classification statuses, in particular, based on a comparison of the classification results to the classification status, and providing the quality measure.

With that, a method to swiftly screen medical databases may be provided which may be used as a quality control tool.

In particular, the quality measure may indicate the number of correctly and/or wrongly classified medical image datasets based on based on the classification results and the classification statuses and/or the indicate correctly and/or wrongly classified medical image datasets based on based on the classification results and the classification statuses.

According to some examples, the classification statuses may be determined based on supplemental data respectively associated with the classified medical image datasets, the supplemental data in particular comprising medical reports associated with the classified medical image datasets. According to some examples, 'determined based on' may comprise providing a natural language processing algorithm configured to identify the classification status in natural language text and inputting the data in the natural language processing algorithm so as to determine the classification statuses.

In particular, according to some examples, the medical image dataset may be subjected to first and/or second classification stages while being acquired in the sense that a corresponding analysis is carried out "on the fly". With that, the medical image datasets may be already screened for being normal while being acquired which may save time and allows to adapt the running image acquisition.

According to other examples, the medical image datasets may be subjected to first and/or second classification stages after having been acquired (after the acquisition has been completed), e.g., by pulling the medical image dataset from a corresponding storage such as the aforementioned PACS.

According to some examples, the first and/or second classification stage comprise detecting one or medical findings and the method further comprises (e.g., in the first and/or second classification stage) classifying the one or more medical findings as non-actionable or actionable and classifying the medical image dataset as normal or not-normal based on the classifying the one or more medical findings as non-actionable or actionable. This has the advantage that non-actionable findings may be recognized with will reduce the number of findings a user has to review. In turn, the amount of work for the user may be reduced and the method is rendered more efficient.

According to an example, classifying the one or more medical findings is based on the supplementary data. This has the advantage that the circumstances for the particular patient may be considered. While certain medical findings may be non-actionable for one patient (e.g., because they relate to anamnestic knowledge) they may be actionable for another patient.

According to an aspect, a system for classifying a medical image dataset comprising an interface unit and a computing unit is provided. The computing unit is configured to receive (or obtain) the medical image dataset showing a body part of a patient from the interface unit. The computing unit is configured to provide (and/or to host and/or to apply) a first classification stage configured to classify the medical image dataset as normal or not-normal. The computing unit is configured to provide (and/or to host and/or to apply) a second classification stage different than the second classification stage configured to classify the medical image dataset as normal or not-normal. The computing unit is configured to subject the medical image dataset to the first classification stage so as to classify the medical image dataset as normal or not-normal. The computing unit is configured to subject the medical image dataset to the second classification stage so as to classify the medical image dataset as normal or not-normal if the medical image dataset is classified as normal in the first classification stage. The computing unit is configured to provide a classification result of the medical image dataset being normal or not-normal via the interface unit.

The computing unit may be realized as a data processing system or as a part of a data processing system. Such a data processing system can, for example, comprise a cloud-computing system, a computer network, a computer, a tablet computer, a smartphone and/or the like. The computing unit can comprise hardware and/or software. The hardware can comprise, for example, one or more processors, one or more memories, and combinations thereof. The one or more memories may store instructions for carrying out the method steps according to embodiments of the invention. The hardware can be configurable by the software and/or be operable by the software. Generally, all units, sub-units or modules may at least temporarily be in data exchange with each other, e.g., via a network connection or respective interfaces. Consequently, individual units may be located apart from each other. Further, the computing unit may be configured as an edge device.

The interface unit may comprise an interface for data exchange with a database for retrieving medical image datasets from the database. The interface unit may be further adapted to interface with one or more users of the system, e.g., by displaying the result of the processing, e.g., any classification result, to the user (e.g., in a graphical user interface).

The systems may be adapted to implement the inventive method in their various aspects for modifying medical image data. The advantages described in connection with the method aspects and examples may also be realized by the correspondingly configured systems' components. Accordingly, the advantages described in connection with the method-aspects and examples are also attributable to the corresponding systems.

According to another aspect, the present invention is directed to a computer program product comprising program elements which induce a computing unit of a system configured for classifying a medical image dataset to perform the steps according to one or more of the above method aspects and examples, when the program elements are loaded into a memory of the computing unit.

According to another aspect, the present invention is directed to a computer-readable medium on which program elements are stored that are readable and executable by a computing unit of a system configured for classifying a medical image dataset according to one or more method aspects and examples, when the program elements are executed by the computing unit.

The realization of embodiments of the invention by a computer program product and/or a computer-readable medium has the advantage that already existing providing systems can be easily adapted by software updates in order to work as proposed by embodiments of the invention.

The computer program product can be, for example, a computer program or comprise another element next to the computer program as such. This other element can be hardware, e.g., a memory device, on which the computer program is stored, a hardware key for using the computer program and the like, and/or software, e.g., a documentation or a software key for using the computer program. The computer program product may further comprise development material, a runtime system and/or databases or libraries. The computer program product may be distributed among several computer instances.

Figure 1:
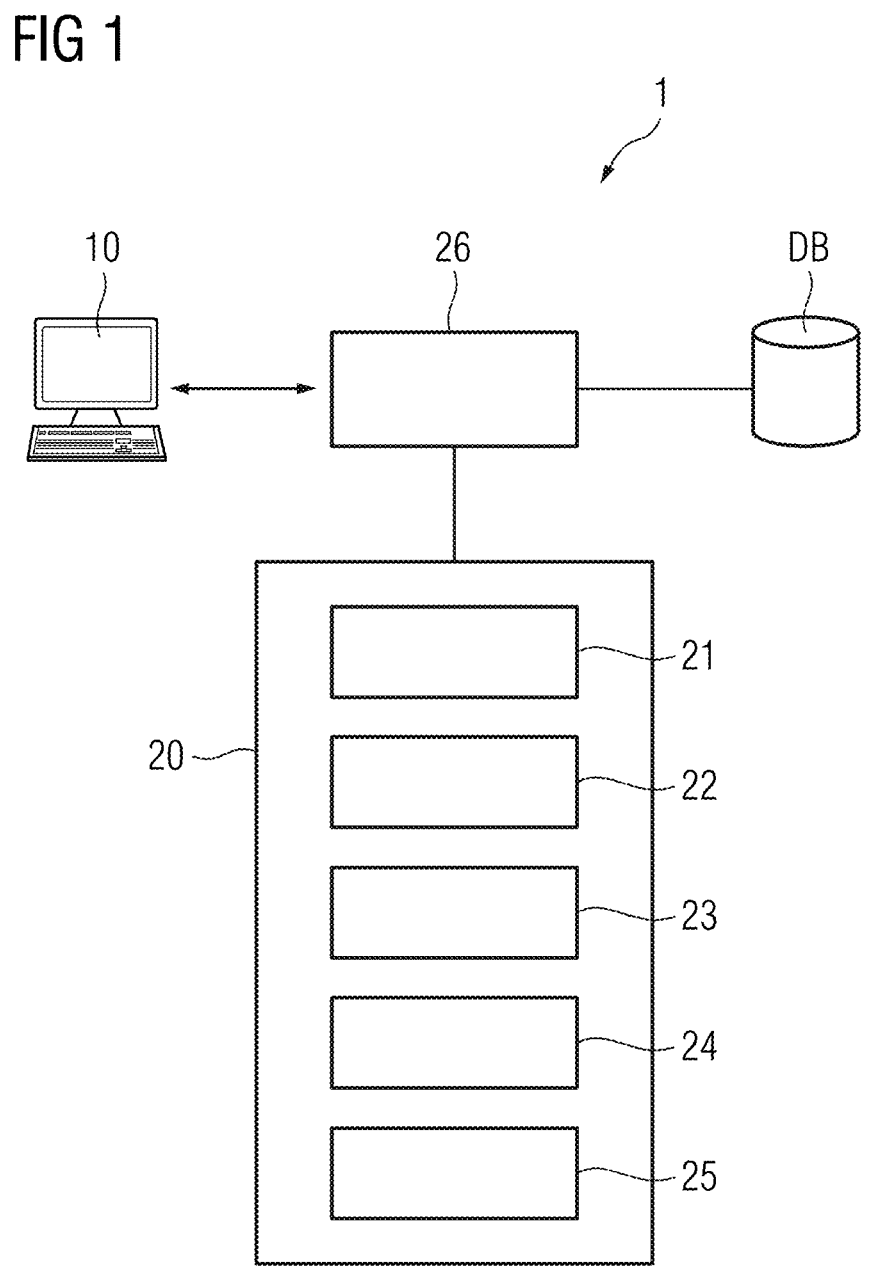

FIG. 1 depicts a system 1 for classifying a medical image dataset MID. System 1 is adapted to perform the methods according to one or more embodiments, e.g., as further described with reference to FIGS. 2 to 6. A user of system 1, according to some examples, may generally relate to a healthcare professional such as a physician, clinician, technician, radiologist, pathologist and so forth.

System 1 comprises a user interface 10 (as part of the interface unit) and a computing unit 20. Further, system 1 may comprise or be connected to a database DB.

The database DB may generally be configured for acquiring and/or storing and/or forwarding medical image datasets MID of one or more patients and, optionally, associated supplementary information SD. The database DB may be embodied by one or more storages. In particular, the database DB may be realized in the form of one or more cloud storage modules. Alternatively, the database DB may be realized as a local or spread storage. According to some examples, the database DB may be formatted according to a medical informatics standard such as the DICOM and/or FHIR standard. This may mean that the database DB and the entries therein comprised encode standardized data identifiers according to the respective standard.

Medical image datasets MID may be three-dimensional image datasets acquired, for instance, using an X-ray system, a computed tomography system or a magnetic resonance imaging system or other systems. The image information may be encoded in a three-dimensional array of m times n times p voxels. Medical images IM may include a plurality of image slices which are stacked in a stacking direction to span the image volume covered by the medical image datasets MID.

Further, medical image datasets MID may comprise two-dimensional medical image data with the image information being encoded in an array of m times n pixels. According to some examples, these two-dimensional medical image data sets MIDS may have been extracted from three-dimensional medical image datasets.

An ensemble of voxels or pixels may be designated as image data of the respective medical image datasets MID in the following. In general, any kind of imaging modalities and scanners may be used for acquiring such image data. Generally, medical image datasets MID show a body part or an anatomical region or an anatomic object of a patient which may comprise various anatomies and organs. Considering the chest area as a body part, medical image datasets MID might, for instance, depict the lung lobes, the rib cage, the heart, lymph nodes, and so forth.

Medical image dataset MID may be formatted according to the DICOM format. DICOM (=Digital Imaging and Communications in Medicine) is an open standard for the communication and management of medical imaging information and related data in healthcare informatics. DICOM may be used for storing and transmitting medical images and associated information enabling the integration of medical imaging devices such as scanners, servers, workstations, printers, network hardware, and picture archiving and communication systems (PACS). It is widely adopted by clinical syndicates, hospitals, as well as for smaller applications like doctors' offices or practices. A DICOM data object consists of a number of attributes, including items such as the patient's name, ID, etc., and also special attributes containing the image pixel data and metadata extracted from the image data.

Supplementary data SD may be any data providing additional information relating to the patient and/or the medical image dataset MID. The supplementary data SD may comprise non-image data or data with mixed-type contents comprising medical images and non-image contents such as text. Non-image data may relate to non-image examination results such as lab data, vital signs records (comprising, e.g., ECG data, blood pressure values, ventilation parameters, oxygen saturation levels) and so forth. Moreover, the supplementary data SD may comprise structured and unstructured reports relating to prior examinations of the patient. Further, the supplementary data SD may comprise personal information of the patient such as gender, age, weight, insurance details, and so forth.

The supplementary data SD may be available in the form of one or more electronic medical reports of the patient.

User interface 10 may comprise a display unit and an input unit. User interface 10 may be embodied by a mobile device such as a smartphone or tablet computer. Further, user interface 10 may be embodied as a workstation in the form of a desktop PC or laptop. The input unit may be integrated in the display unit, e.g., in the form of a touch screen. As an alternative or in addition to that, the input unit may comprise a keyboard, a mouse or a digital pen, a microphone and any combination thereof. The display unit may be configured for displaying a representation of the medical image dataset MID and/or a worklist WL of tasks for assessing medical image datasets MID and/or medical reports associated with medical image datasets MID.

User interface 10 may further comprise an interface computing unit configured to execute at least one software component for serving the display unit and the input unit in order to provide a graphical user interface GUI for allowing the user to input select items from the worklist WL, process medical image datasets, and edit medical reports. In addition, the interface computing unit may be configured to communicate with the computing unit 20 for receiving the worklist WL, medical image datasets MID or renderings thereof, supplementary information, and/or classification result of medical image datasets being normal or not normal. The user may activate the software component via user interface 10 and may acquire the software component, e.g., by downloading it from an internet application store. According to an example, the software component may also be a client-server computer program in the form of a web application running in a web browser. The interface computing unit may be a general processor, central processing unit, control processor, graphics processing unit, digital signal processor, three-dimensional rendering processor, image processor, application specific integrated circuit, field programmable gate array, digital circuit, analog circuit, combinations thereof, or other now known devices for processing image data. User interface 10 may also be embodied as a client.

Computing unit 20 may comprise sub-units 21-25 configured to process medical image datasets MID in order to classify these as normal or not-normal in order to provide a classification result CR, I-CR and, thus, provide an indication for a medical diagnosis.

Computing unit 20 may be a processor. The processor may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data. The processor may be single device or multiple devices operating in serial, parallel, or separately. The processor may be a main processor of a computer, such as a laptop or desktop computer, or may be a processor for handling some tasks in a larger system, such as in the medical information system or the server. The processor is configured by instructions, design, hardware, and/or software to perform the steps discussed herein. The computing unit 20 may be comprised in the user interface 10. Alternatively, computing unit 20 may be separate from user interface 10. Computing unit 20 comprise a real or virtual group of computers like a so called 'cluster' or 'cloud'. Such server system may be a central server, e.g., a cloud server, or a local server, e.g., located on a hospital or radiology site. Further, processing system 20 may comprise a memory such as a RAM for temporally loading the medical image datasets MID and any supplementary information from the database DB. According to some examples, such memory may as well be comprised in user interface 10.

Sub-unit 21 is a data retrieval module or unit. It is configured to access and search the database DB for the medical image datasets MID. Specifically, sub-unit 21 may be configured to formulate search queries and parse them to the database DB. In the same manner, sub-unit 21 may be configured to retrieve supplementary data SD for the patient.

Sub-unit 22 may be conceived as a quality assessment module or unit configured to scrutinize that the medical image dataset MID is suited for the ensuing automated classification. To this end, sub-unit 22 may be configured to determine and assess one or more predefined quality parameters of the medical image dataset MID. Further, sub-unit 22 may be configured to check if the field of view of the medical image dataset MID matches the diagnostic task to be performed based on the medical image dataset MID.

Sub-unit 23 may be conceived as a first classification module or unit configured to define and apply a first classification stage CS1 in order to classify the medical image dataset MID. According to some examples, the first classification module 23 is configured to verify that the medical image dataset is normal, i.e., only shows image data which is, in a medical sense, normal. Specifically, sub-unit 23 may be configured to select and run accordingly configured classification algorithms TF-N, C-TF-N according to some examples. To this end, sub-unit 23 may access or serve a storage or library of classification algorithms. Such library may be a collection of trained functions TF-N, C-TF-N which are specifically configured to identify normal, i.e., not actionable features in a medical image dataset MID.

Sub-module 24 may be conceived as a second classification module or unit configured to define and apply a second classification stage CS2 in order to classify the medical image dataset MID. According to some examples, the first classification module 24 is configured to determine if the medical image dataset MID contains any specific medical abnormalities. Specifically, sub-unit 24 may be configured to select and run accordingly configured classification algorithms DA-NN, C-DA-NN according to some examples. To this end, sub-unit 24 may access or serve a storage or library of classification algorithms DA-NN, C-DA-NN. Such library may be a collection of trained classifiers or detection algorithms DA-NN which are specifically configured to identify abnormal features in a medical image dataset MID which require an expert review.

Sub-unit 25 may be conceived as a post-processing module or unit. Sub-unit 25 may be configured to use the classification results CR, I-CR provided by the first and second classification stages CS1, CS2 to provide actionable results for the user. According to some examples, such results may comprise an updated worklist WL in which the medical image dataset MID is given a certain priority based on the classification results CR, I-CR. Additionally or alternatively, sub-unit 25 may be configured to automatically generate or pre-configure one or more medical reports MR for the medical image dataset MID based on the classification results CR, I-CR. Further, sub-unit 25 may be configured as a user interaction module or unit. Sub-unit 25 may be configured to provide a graphical user interface GUI to a user for displaying to the user via the user interface 10. The graphical user interface GUI can be configured to support the presentation of the provided classification result CR, I-CR, the worklist WL, and/or any artefact created on the basis of the classification results CR, I-CR such as medical reports MR.

The designation of the distinct sub-units 21-25 is to be construed by way of example and not as a limitation. Accordingly, sub-units 21-25 may be integrated to form one single unit (e.g., in the form of "the computing unit") or can be embodied by computer code segments configured to execute the corresponding method steps running on a processor or the like of Computing unit 20. The same holds true with respect to the interface computing unit. Each sub-unit 21-25 and the interface computing unit may be individually connected to other sub-units and/or other components of the system 1 where data exchange is needed to perform the method steps.

Computing unit 20 and the interface computing unit together may constitute the computing unit of the system 1.

Of note, the layout of this computing unit, i.e., the physical distribution of the interface computing unit and sub-units 21-25 is, in principle, arbitrary. For instance, sub-unit 21 (or individual elements of it or specific algorithm sequences) may likewise be localized in user interface 10. The same holds true for the other sub-units 21-25. Specifically, computing unit 20 may also be integrated in user interface 10. As already mentioned, computing unit 20 may alternatively be embodied as a server system, e.g., a cloud server, or a local server, e.g., located on a hospital or radiology site. According to some implementations, user interface 10 could be designated as a "frontend" or "client" facing the user, while computing unit 20 could then be conceived as a "backend" or server. Communication between user interface 10 and computing unit 20 may be carried out using the https-protocol, for instance. The computational power of the system may be distributed between the server and the client (i.e., user interface 10). In a "thin client" system, the majority of the computational capabilities exists at the server. In a "thick client" system, more of the computational capabilities, and possibly data, exist on the client.

Individual components of system 1 may be at least temporarily connected to each other for data transfer and/or exchange. User interface 10 communicates with processing system 20 via (data) interface 26 to exchange, e.g., the medical report MR, the worklist WL or any user input made. Further, computing unit 20 may communicate with the database DB in order to medical image datasets MID, P-MID via the data interface 26. Data interface 26 for data exchange may be realized as hardware- or software-interface, e.g., a PCI-bus, USB or fire-wire. Data transfer may be realized using a network connection. The network may be realized as local area network (LAN), e.g., an intranet or a wide area network (WAN). Network connection is preferably wireless, e.g., as wireless LAN (WLAN or Wi-Fi). Further, the network may comprise a combination of different network examples. Interface 26 for data exchange together with the components for interfacing with the user be regarded as constituting an interface unit of system 1.

Figure 3:
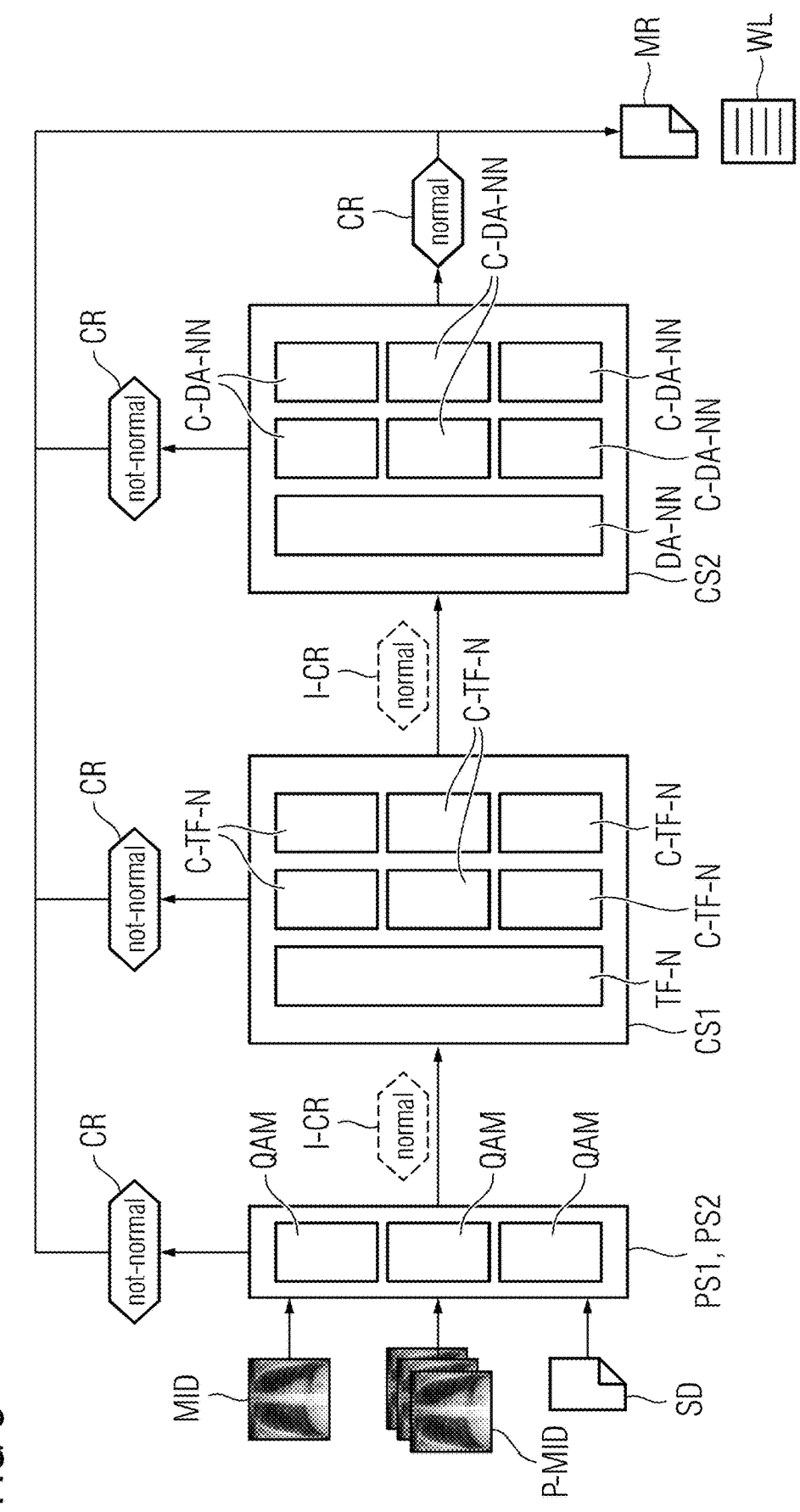
FIG. 3 schematically depicts an exemplary data flow diagram in connection with a method for classifying a medical image dataset according to an embodiment.

FIG. 2 depicts a method for classifying a medical image dataset MID according to an embodiment. Corresponding data streams are illustrated in FIG. 3. The method comprises several steps. The order of the steps does not necessarily correspond to the numbering of the steps but may also vary between different embodiments of the present invention. Further, individual steps or a sequence of steps may be repeated.

At step S10, the medical image dataset MID is received. This may involve selecting the medical image dataset MID from a plurality of cases, e.g., stored in the database DB. The selection may be performed manually by a user, e.g., by selecting appropriate image data in a graphical user interface running in the user interface 10. Alternatively, the medical image dataset MID may be provided to the computing unit by a user by way of uploading the medical image dataset MID to the computing unit.

In optional sub-step S11, a prior medical image dataset P-MID may be obtained. The prior medical image dataset P-MID may show the same body part of the same patient as the medical image dataset MID but a different point in time. Obtaining may mean querying the database DB for one or more prior medical image datasets P-MID, for instance, based on a patient ID of the patient.

In optional sub-step S12, supplemental data SD may be obtained for the medical image dataset MID. The supplemental data SD may comprise medical reports MR, demographic information of the patient, a medical history of the patient, a diagnostic task to be performed based on the medical image dataset MID or the like. Obtaining the supplemental data SD may comprise querying the database DB for supplementary data SD, e.g., based on the patient ID of the patient.

Further, step S10 may comprise one or two optional pre-classification stages PS1, PS2, which may form the first or second classification stage CS1, CS2 or which may be comprised in the first or second classification stage CS1, CS2. As a non-limiting alternative, on or more of the optional pre-classification stages PS1, PS2 may precede the classification stages CS1, CS2 as shown in FIG. 3.

A first pre-classification stage PS1 is based on an assessment if the medical image dataset MID matches the clinical context and/or the diagnostic task as derivable from the supplementary data SD. Specifically, at step S13, a region of interest or (compartment of relevance) may be determined based on the supplementary data SD. For instance, if the diagnostic task relates to the lung of the patient, the region of interest is the lung. Step S13 may comprise applying a natural language processing algorithm to the supplementary data SD so as to determine the compartment (s) of relevance. Compartment in this respect may be an organ or anatomical structure of the patient. In a next step S14, the medical image dataset MID may be segmented to identify one or more compartments depicted in the image data of the medical image dataset MID. Taking a chest CT of the patient as an example, this may be the bones, lung, liver, heart and so forth. In a next step S15, it may be checked if the region of interest is reflected in the compartments recognized in the medical image dataset MID. On that basis it may be checked at step S16 if the medical image dataset MID matches the clinical context. If so, the medical image dataset MID may be regarded as normal in this regard and a corresponding intermediate classification result I-CR may be provided and the method may proceed with the next steps. If not, the medical image dataset at step S16 may be classified as not-normal as a classification result CR as it obviously should be brought to the attention of the user.

A second pre-classifications stage PS2 is based on automatically determining an image quality. Specifically, at step S17, an image quality value may be derived from the medical image dataset MID. For instance, it may be determined, if the signal to noise ratio is acceptable, if the orientation and/or field of view are acceptable, if the inspiration cycles are correct, if an acceptable penetration depth was reached, if reasonable post-processing functions have been used (such as appropriate convolution kernels in case of CT imaging), if the medical image dataset was acquired using a reasonable sequence protocol (in case of MR imaging), and so forth. The corresponding classification stage PS2 may comprise a plurality of quality assessment modules QAM which are respectively configured to extract individual quality measures from the medical image dataset MID. The individual quality measures may be aggregated to form the image quality value. At step S18, it may then be determined if the image quality is sufficient for confidently classifying the medical image dataset MID as normal. For instance, the image quality value may be compared to a predetermined threshold. If the image quality is not sufficient, the medical image dataset is classified as not-normal as a classification result CR in step S18. If the quality is sufficient, the medical image dataset MID may be classified as normal in this regard and a corresponding intermediate classification result I-CR may be provided and the classification may proceed to the next stage.

Step S20 is directed to provide the first classification stage CS1. For instance, the first classification stage CS1 may be provided by holding it available in a memory of the processing unit, for instance, as executable computer code.

According to the embodiment, the first classification stage CS1 is configured to actively confirm that the medical image dataset MID is normal. In other words, the first classification stage CS1 may be conceived as a normal "rule-in" stage.

The first classification stage CS1 may comprise one or more individual (normal) classification algorithms TF-N, C-TF-N. The classification algorithms TF-N, C-TF-N, for instance, may comprise one or more trained classifiers TF-N, C-TF-N, which have been configured for specific aspects of classifying a medical image dataset MID as normal. While some classification modules TF-N may be configured to classify the medical image dataset MID as a whole, others C-TF-N may be configured to classify parts or compartments of the medical image dataset. For instance, there may be a plurality of specifically configured trained functions C-TF-N each having been configured to classify a specific compartment of a medical image dataset MID as normal. Further, the classification algorithms TF-N, C-TF-N may be configured to take prior information into account such as prior medical image datasets P-MID.

Step S30 is directed to provide the second classification stage CS2. For instance, the second classification stage CS2 may be provided by holding it available in a memory of the processing unit, for instance, as executable computer code.

According to the embodiment, the second classification stage CS2 is configured to actively search for abnormalities in the medical image dataset MID. In other words, the second classification stage CS2 may be conceived as an abnormality "rule-out" stage.

Like the first classification stage CS1, the second classification stage CS2 may comprise one or more individual classification algorithms DA-NN, C-DA-NN—which are configured to detect abnormalities in medical image datasets. The classification algorithms DA-NN, C-DA-NN, for instance, may comprise one or more trained detection algorithms DA-NN, C-DA-NN which have been configured to detect specific abnormalities in a medical image dataset MID. While some classification algorithms DA-NN may be configured to consider the medical image dataset MID as a whole, others C-DA-NN may be specifically configured to search for abnormalities in parts or compartments of the medical image dataset MID. For instance, there may be a plurality of specifically configured trained functions C-DA-NN each having been configured to process a specific compartment of a medical image dataset or to find specific abnormalities such as lesions, fractures, foreign bodies, hernia, pneumonia, pneumothorax, scoliosis etc. Further, the classification algorithms DA-NN, C-DA-NN may be configured to take prior information into account such as prior medical image datasets P-MID.

At step S40, the first classification stage CS1 is applied to the medical image dataset MID in order to classify the medical image dataset MID as normal or not-normal.

As will be outlined in the following, the classification by applying the first classification stage CS1 may involve several optional image processing sub-steps of the medical image dataset MID according to the respective configuration of the classification stage CS1. The following steps may be performed individually or in arbitrary combinations. The (intermediate) classification results I-CR of individual sub-steps may be aggregated to obtain the overall classification result CR of the medical image dataset MID. Thereby, according to some examples, the overall classification result CR is only set to normal if the all of the individual sub-steps applied yielded a normal intermediate classification result I-CR. In other words, the overall classification result CR is set to not-normal as soon as one of the individual sub-steps could not verify that the medical image dataset MID is normal.

Optionally, at step S41, the medical image dataset MID may be input into a classification algorithm TF-N of the first classification stage CS1 as to determine if the medical image dataset MID is normal. Specifically, according to some examples, the classification algorithm TF-N may be a trained classifier which has been configured to take in the medical image dataset MID as whole and output a classification result indicating if the medical image dataset MID, as a whole, is normal.

Optional steps S42 and S43 deal with a compartment-wise classification. At step S42 the medical image dataset MID is segmented by applying a corresponding segmentation algorithm. For instance, this may involve identifying a compartment within the medical image dataset MID and delineating the corresponding image data, e.g., in a segmented dataset. Next, at step S43, the segmented dataset is classified as normal or not-normal.

Optional steps S44 and S45 are directed to select an appropriate classification algorithm C-TF-N or trained classifier from the available algorithms in the first classification stage CS1. The selection may take place at step S44, while, at step S45, the selected classification algorithm C-TF-N is applied to the medical image dataset MID so as to provide a corresponding classification result CR, I-CR. According to some examples, the classification algorithm C-TF-N are selected according to the compartment (s) identified at step S42.

Optional step S46 is directed to factor in prior information in the classification. Specifically, step S46 is configured to classify the medical image dataset MID additionally based on a prior medical image dataset P-MID and/or a prior medical report of the patient. According to some examples, the classification algorithms TF-N, C-TF-N used in step S46 may be configured to infer one or more prior findings from the prior information and/or determine a change from the prior information to the medical image dataset MID. Step S46 may be applied on the medical image dataset MID as whole or be performed compartment-wise.

At optional step S47, a classification result CR, I-CR may be provided additionally based on the supplementary data SD. With that, if the supplementary data SD comprises indications of potential abnormalities or nonsuspicious parts, the medical image dataset MID may be specially checked on that basis. According to some examples, a corresponding classification algorithm TF-N, C-TF-N may comprise a natural language processing algorithm configured to extract corresponding information from the supplementary data SD.

At optional sub-step S48, a sensitivity of the classification stage CS1 (or any applicable classification algorithm TF-N, C-TF-N) may be adjusted based on the supplementary information. If, for instance, a prior report indicates a lung lesion, the sensitivity of a corresponding trained classifier TF-N, C-TF-N may be increased.

Optional steps S49 and S410 can be conceived as a confidence filter with which all intermediate classification results I-CR of the medical image dataset MID being normal are checked for their confidence levels (step S49). If the confidence level is too low, the normal-classification is overruled and set to not normal (step S410).

At step S50, the second classification stage CS2 is applied to the medical image dataset MID in order to classify the medical image dataset MID as normal or not-normal and provide a corresponding classification result CR, I-CR.

At optional step S51 it is checked if the classification result of the classification result CR, I-CR of the first classification stage CS1 is normal or not-normal. According to some examples, the second classification stage CS2 is only applied if the classification result CR, I-CR of the first classification stage CS1 is normal. With that, the second classification stage CS2 may be seen as a double check to safeguard a normal classification result I-CR.

As will be outlined in the following, the classification by applying the second classification stage CS2 likewise may involve several optional image processing sub-steps of the medical image dataset MID according to the respective configuration of the classification stage CS2. The following steps may be performed individually or in arbitrary combinations. The classification results I-CR of individual sub-steps may be aggregated to obtain the overall classification result CR of the medical image dataset MID in the second classification stage CS2. Thereby, according to some examples, the overall classification result CR is only set to normal if all of the individual sub-steps applied did not retrieve any abnormalities. In other words, the overall classification result CR is set to not-normal as soon as one of the individual sub-steps could identified an abnormality in the medical image dataset MID.

Optionally, at step S52, the medical image dataset MID may be input into a classification algorithm DA-NN of the second classification stage CS2 as to determine if the medical image dataset MID comprises abnormalities. Specifically, according to some examples, the classification algorithm DA-NN may be a trained classifier which has been configured to generally identify abnormalities in the medical image dataset MID as a whole.

Optional steps S53 and S54 deal with a compartment-wise classification in a similar manner as in steps S42 an S43.

Optional steps S55 and S56 are directed to select an appropriate classification algorithm C-DA-NN from the plurality of detection algorithms DA-NN, C-DA-NN available in the second classification stage CS2. Apart from that, steps S55 and S56 correspond to steps S44 and S45.

Optional step S57 is directed to consider prior information in the classification. Specifically, step S57 is configured to classify the medical image dataset MID additionally based on a prior medical image dataset P-MID and/or a prior report of the patient. According to some examples, the classification algorithm (s) DA-NN, C-DA-NN used in step S57 may be configured to infer one or more prior findings from the prior information and/or determine a change from the prior information to the medical image dataset MID. Step S57 may be applied on the medical image dataset MID as whole or be performed compartment-wise.

At optional step S58, a classification result CR, I-CR may be provided additionally based on the supplementary data SD. With that, if the supplementary data SD comprises indications of potential abnormalities, the medical image dataset MID may be specially checked for these potential abnormalities. According to some examples, a corresponding classification algorithm DA-NN, C-DA-NN may comprise a natural language processing algorithm configured to extract corresponding information (i.e., the aforementioned indications) from the supplementary data SD.

At optional sub-step S59, a sensitivity of the classification stage CS2 (or any applicable classification algorithm DA-NN, C-DA-NN) may be adjusted based on the supplementary data SD. If, for instance, a prior report indicates a lung lesion, the sensitivity of a corresponding trained classifier C-DA-NN may be increased.

Optional steps S510 and S511 can again be conceived as a confidence filter which may be configured in the same way as in steps S49 and S410.

At optional step S60, the classification result CR is provided. This may involve showing the classification result CR to the user in the user interface 10. Alternatively or additionally, this may involve providing the classification result CR for further processing, e.g., by one or more automated processing algorithms.

For instance, at an optional sub-step S61, the classification result CR may be provided to a scheduling algorithm which is outputting a worklist WL for user. Specifically, the scheduling algorithm may be configured to modify the worklist WL based on the classification result CR. This may involve organizing the worklist WL into normal and not-normal cases. Alternatively or additionally, this may comprise prioritizing not-normal cases so that these show up at the top portions of the worklist WL. According to some examples, this may even involve removing medical image datasets MID from the worklist WL if they are normal as they do not require a review by the user. According to some examples, a removal of a medical image dataset MID from the worklist WL may be made dependent on a confidence value. Only if the confidence value of the classification result CR indicates a sufficiently high confidence of a normal classification result CR, the medical image dataset MID is removed. To this end, the confidence value may be compared to a predetermined threshold (which may be more restrictive than the one used at steps S49/S410 or S510/S511). Only if the medical image dataset MID is securely classified as normal, it may be removed from the worklist WL.

At optional steps S62 and S63, the classification result CR and also the intermediate classification results I-CR may be used to automatically generate a medical report MR. Thereby, step S62 comprises generating the medical report MR and step S63 comprises providing the medical report MR. For instance, the classification result CR, I-CR, in step S62, may be used to select an appropriate report template. Thereby, different templates may come into questions if the medical image dataset MID is normal as compared to a case where it is not. Further, step S62 may comprise pre-filling the medical report based on the classification result. For instance, any abnormalities found at step S40 may be indicated in the medical report MR.

At step S63, the medical report MR generated at step S62 is provided. The way the medical report MR is provided in step S63 may again be made dependent on the classification result CR, I-CR. According to some examples, if the classification result CR is normal and, optionally, has a sufficiently high confidence value, the medical report MR may be archived without the user having to sign off. Thereby, this route may coincide with the medical image dataset MID being removed from the worklist WL at step S61. If the classification result CR is not-normal or normal but with too low a confidence value, the report MR may be provided to the user for further review.

Figure 4:
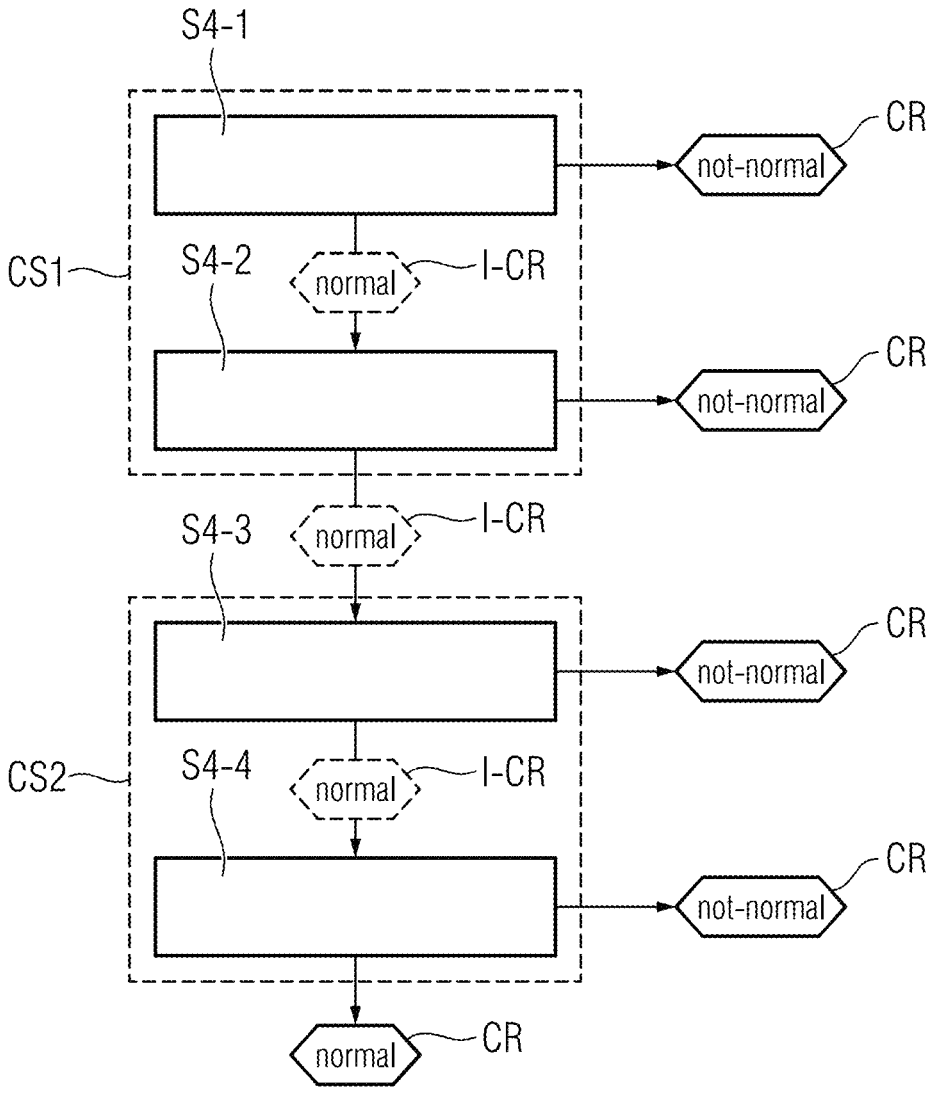
FIG. 4 schematically depicts a flowchart of a method for classifying a medical image dataset according to an embodiment.

FIG. 4 depicts a method for classifying a medical image dataset MID according to an embodiment. Corresponding data streams are illustrated in FIG. 3. The method comprises several steps. The order of the steps does not necessarily correspond to the numbering of the steps but may also vary between different embodiments of the present invention. Further, individual steps or a sequence of steps may be repeated.

Specifically, FIG. 4 shows an embodiment exemplifying how individual steps as introduced in connection with FIG. 2 may be combined.

At a first step S4-1, it is determined at a level of the entire image data if the medical image dataset MID is normal. To this end, the medical image dataset MID may be input in a correspondingly configured trained function TF-N as described in connection with step S41. If the medical image dataset MID is classified as normal with sufficient certainty, the method proceeds to the next step S4-2. If the medical image dataset cannot be classified as normal (either because it is not normal or because the confidence value of the normal classification is too low) the processing terminates and provides a classification result CR of the medical image dataset MID being not-normal. Optionally, prior information may be considered at step S4-1, for instance, as described in connection with step S46.

At step S4-2, it may be determined if individual compartments of the medical image dataset MID are normal. To this end, the medical image dataset MID may be segmented into compartments and the corresponding image data of the compartments may be input into correspondingly configured trained functions C-TF-N. Thereby, the processing of step S4-2 may comprise steps S42 and S43. Optionally, prior information may also be considered at step S4-2, for instance, as described in connection with step S46. If every compartment is classified as normal with sufficient certainty, the method proceeds to the next step S4-3. Otherwise, the classification terminates at step S4-2 and provides a classification result CR of the medical image dataset MID as not-normal.

At step S4-3, abnormalities are actively detected. This may involve inputting the medical image dataset MID in a trained function DA-NN configured to detect general abnormalities in medical image datasets (e.g., according to step S52). Optionally, priors may be considered at step S4-3, for instance, as described in connection with step S57. If no abnormalities were found, the medical image dataset is considered normal and the processing proceeds with step S4-4. Otherwise, the classification terminates and provides the classification result CR of the medical image dataset MID being not-normal.

Step S4-4 constitutes another step in which abnormalities are actively detected. Thereby, step S4-4 may be configured to detect specific abnormalities. To this end, step S4-4 may apply in principle known computer aided detection functions C-DA-NN to the medical image dataset MID which may be configured to detect certain kinds of abnormalities in specific compartments, such as lung nodules in image data of the lung of a patient. Accordingly, step S4-4 may comprise a segmentation process, for instance, as described in connection with steps S53 and S54. Also in step S4-4, prior information may be considered as described in connection with step S57. If no abnormalities were found in step S4-4, the medical image dataset MID is finally classified as normal. Otherwise, the medical image dataset is classified as not-normal.

In FIG. 4, it is indicated that steps S4-1 and S4-2 are comprised in the first classification stage CS-1 and steps S4-3 and S4-4 are comprised in the second classification stage CS2. However, it should be noted that this mapping is arbitrary. In principle, also the steps S4-1, S4-2, S4-3, S4-4 individually could be regarded as classification stages or steps S4-1, S4-2, S4-3, S4-4 may be comprised in one classification stage.

Figure 5:
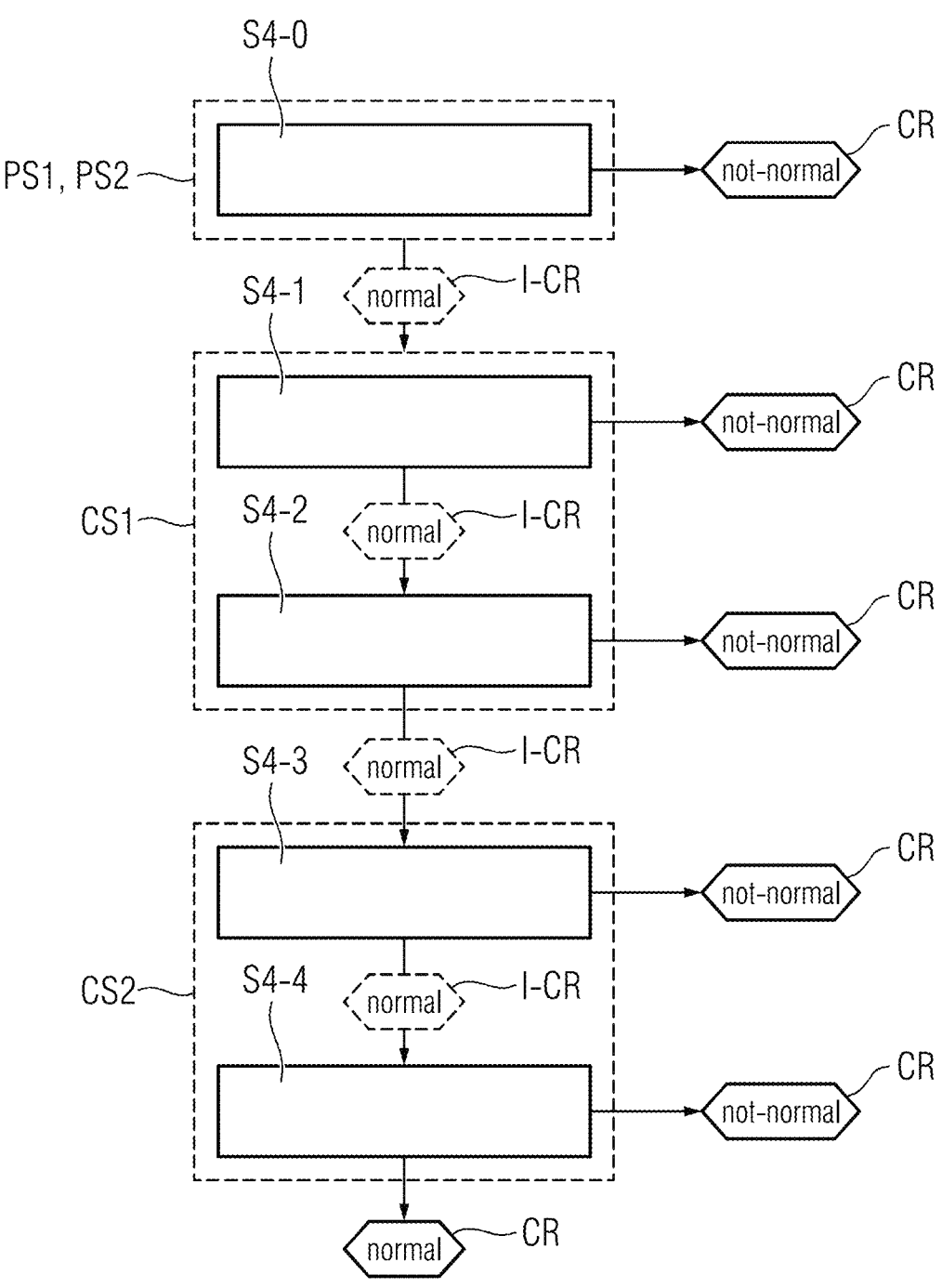
FIG. 5 schematically depicts a flowchart of a method for classifying a medical image dataset according to an embodiment.

FIG. 5 depicts a method for classifying a medical image dataset MID according to an embodiment. Corresponding data streams are illustrated in FIG. 3. The method comprises several steps. The order of the steps does not necessarily correspond to the numbering of the steps but may also vary between different embodiments of the present invention. Further, individual steps or a sequence of steps may be repeated.

The example shown in FIG. 5 corresponds to the one shown in FIG. 4. However, it comprises another classification step S4-0 which may be regarded as pre-classification step to make sure that the medical image dataset MID and the supplementary data SD (if any) are of sufficient quality and consistency for an automated classification into normal and not-normal. Specifically, step S4-0 may comprise the pre-classification stages PS1 and/or PS2 as described in connection with step S10.

With that, it may be automatically identified if proper imaging protocols were followed during acquisition of the medical image dataset MID. This may ensure proper coverage of the exam to answer the clinical question. Similarly, it may be made sure that the detector is not over- or under-penetrated, that the patient inspired properly for a clear picture of the lung-field, and/or that the patient is not excessively rotated and a proper view of the anatomy is obscured. If the medical image dataset MID fails to meet one or more quality criteria of step S4-0, the medical image dataset MID is classified as not-normal. Otherwise, the processing may proceed with the first normal "rule-in" of step S4-1.

It should be noted that step S4-0 may also be integrated in one of the classification stages CS1 and/or CS", although being illustrated as a separate stage in FIG. 5 for clarity reasons.

Figure 6:
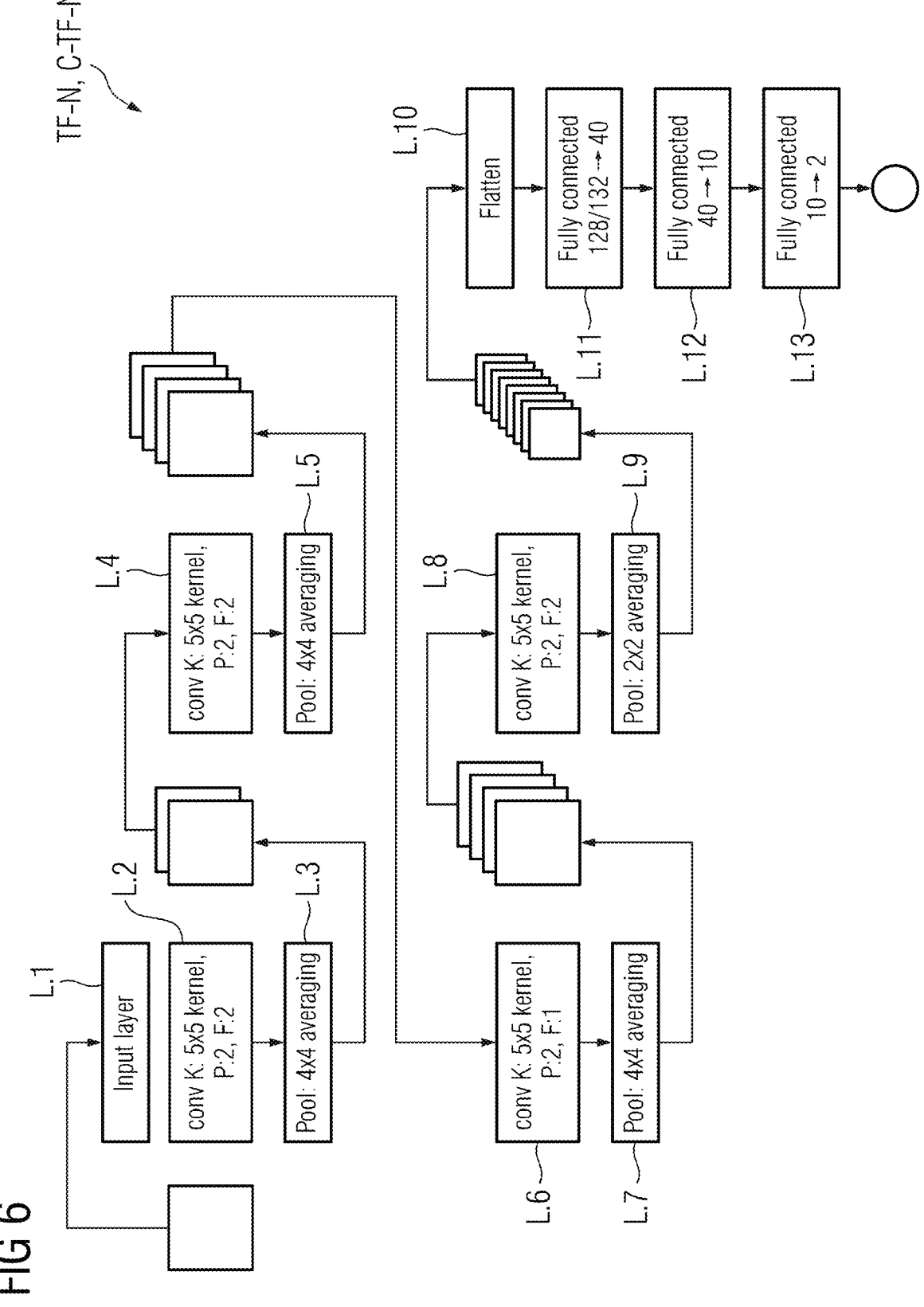
FIG. 6 schematically depicts a trained function for classifying a medical image dataset according to an embodiment.

FIG. 6 schematically shows a trained function TF-N, DA-NN, C-TF-N, C-DA-NN according to an embodiment.

In principle, any known classification and detection functions may be used for determining that the medical image dataset MID is normal and for finding abnormalities in medical image dataset MID. In particular, this applies if specific abnormalities are to be detected in the compartments depicted in the medical image dataset MID (c.f., step S4-3, for instance) as there already exists a plethora of well proven and certified algorithms for these purposes (for corresponding patent literature c.f.: US 2009/0 092 300 A1, US 2009/0 067 693 A1, or US 2016/0 321 427 A1, for instance).

As regards the verification that certain image data is normal, i.e., only presents non-actionable features, the inventors propose using a convolutional neural network, in particular, a deep convolutional neural network, for the trained function TF-N, C-TF-NN as displayed in FIG. 6. The convolutional neural network comprises convolutional layers, pooling layers and fully connected layers.

In the input layer L.1, there is one node for each pixel of the medical image dataset MID or any segmented compartment, each pixel having one channel (the respective intensity value). After the input layer, there are four convolutional layers L.2, L.4, L.6, L.8, each of the four convolutional layers followed by a pooling layer L.3, L. 5, L.7, L.9. For each of the convolutional layers, a 5×5 kernel is used (indicated by "K: 5×5") with a padding of 2 (indicated by "P: 2") and either one or two filters/convolutional kernels (indicated by "F: 1" or "F: 2"). Furthermore, there are four pooling layers L.3, L.5, L.7, L.9, the first three layers L.3, L.5, L.7 implementing an averaging operation over patches of size 4×4, and the last pooling layer L.9 implementing a maximum operation over patches of size 2×2. Within FIG. 6 an additional layer L.10 is indicated that flattens the input images (i.e., taking the 8 images of size 4×4 and giving a vector of 128 entries). However, this layer is not relevant for the actual calculation. The last layers of the network are three fully connected layers L.11, L.12, L.13, the first fully connected layer having 128 input and 40 output nodes, the second fully connected layer L.12 having 40 input and 10 output nodes, and the third fully connected layer L.13 having 10 input and one output node, wherein the output node forms the output layer of the whole trained function TF-N. The value of the first node of the output layer corresponds to the probability (or confidence) of the input medical image dataset MID being normal.

In principle, a similar network may be provided for detecting unspecific abnormalities in the medical image dataset MID with the corresponding detection algorithm DA-NN, C-DA-NN. In that case, the third fully connected layer L.13 may have two output nodes, one for providing the probability (or confidence) of the medical image dataset MID being not-normal, and the other node outputting the location and/or size of the features within the medical image dataset MID which constitutes an actionable feature.

Specifically, trained functions TF-N, C-TF-NN which are to be configured to identify normal image data may be trained on a large cohort (millions) of exams without clinically actionable disease. This provides the framework with a global picture of a non-actionable exam. To identify such cases with requiring an expert involvement, domain-specific language models may be used to automatically parse a medical database T-DB for cases suited to train the system in a self-supervised manner. For instance, the language model may be used to automatically label medical image datasets in the database T-DB as normal, e.g., based on medical reports corresponding to the image dataset. An advantage of this procedure is that normal image datasets which predominate in usual medical databases can automatically be used for the training process without requiring an expert annotation.

Another kind of trained classifier TF-N, C-TF-NN may learn non-actionable features of individual compartments. This task can be achieved in a similar fashion using compartmentalized self-supervised learning or other suitable techniques based on segmenting the medical image datasets MID.

Finally, to ensure that critical and life-threatening yet challenging findings are not overlooked, an abnormality detection algorithm DA-NN may be trained based on curated training data which had been annotated by experts.

It is to be noted that the split between distinct trained functions TF-N, C-TF-N, DA-NN, C-DA-NN and detection algorithms made in some parts of the description is to be conceived by way of example and not as limitation. According to some examples, the trained functions TF-N, C-TF-N, DA-NN, C-DA-NN and detection algorithms may also be embodied as branches of an overarching network architecture.

For the actual training process, the available training medical image datasets (either expert-annotated or automatically labeled) may split into training data (e.g., 320 datasets from 500 datasets in total), validation data (e.g., 80 datasets) and test data (e.g., 100 datasets). For training the trained functions TF-N or detection algorithms DA-NN, backpropagation may be used based on a cost function L (x, y1)=|M (x)1−y1|2, wherein x denotes an input medical image dataset MID and y1 denotes whether the respective patient is normal. In the same way additional outputs such as a location and/or size of the actionable features within the medical image dataset MID may be taken into account. Furthermore, M(x) denotes the result of applying the machine learning model to the input medical image x.

Based on the validation set, the best performing machine learning model out of several machine learning models (with different hyperparameters, e.g., number of layers, size and number of kernels, padding etc.) may be selected. The specificity and the sensitivity may then be determined based on the test set.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The expression "a number of" means "at least one". The mention of a "unit" or a "device" does not preclude the use of more than one unit or device. The expression "a number of" has to be understood as "at least one".

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element (s) or feature (s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/

DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

Computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

Shared memory hardware encompasses a single memory device that stores some or all code from multiple modules. Group memory hardware encompasses a memory device that, in combination with other memory devices, stores some or all code from one or more modules.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Wherever meaningful, individual embodiments or their individual aspects and features can be combined or exchanged with one another without limiting or widening the scope of the present invention. Advantages which are described with respect to embodiments of the present invention are, wherever applicable, also advantageous to other embodiments of the present invention.

The invention claimed is:

1. A computer-implemented method for classifying a medical image dataset, the method comprising:

receiving the medical image dataset showing a body part of a patient;

providing a first classification stage configured to classify the medical image dataset as normal or not-normal;

providing a second classification stage different than the first classification stage configured to classify the medical image dataset as normal or not-normal;

subjecting the medical image dataset to the first classification stage to classify the medical image dataset as normal or not-normal; and subjecting the medical image dataset to the second classification stage to classify the medical image dataset as normal or not-normal if the medical image dataset is classified as normal by the first classification stage, wherein at least one of the first classification stage or the second classification stage includes segmenting at least one compartment from the medical image dataset to define a segmented dataset, at least one of the first classification stage or the second classification stage is configured to independently classify i) image data of the medical image dataset as normal or not-normal and ii) image data of the segmented dataset as normal or not-normal, and the medical image dataset is classified as normal if the image data of the medical image dataset is classified as normal and the image data of the segmented dataset is classified as normal.

2. The method of claim 1, wherein:

the first classification stage comprises inputting the medical image dataset to a first trained classifier configured to determine that the medical image dataset is normal, and the second classification stage comprises inputting the medical image dataset to a second trained classifier different than the first trained classifier, the second trained classifier configured to recognize medical abnormalities in medical image datasets.

3. The method of claim 2, further comprising:

obtaining a prior medical image dataset, the prior medical image dataset showing the body part of the patient at a different point in time as the medical image dataset, wherein at least one of the first classification stage or the second classification stage is configured to classify the medical image dataset as normal or not-normal further based on the prior medical image dataset.

4. The method of claim 3, further comprising:

obtaining at least one image quality parameter for the medical image dataset; and classifying the medical image dataset as not-normal based on the at least one image quality parameter.

5. The method of claim 4, further comprising:

obtaining supplementary data associated with the medical image dataset, wherein at least one of the first classification stage or the second classification stage are configured to classify the medical image dataset further based on the supplementary data.

6. The method of claim 1, wherein at least one of the first classification stage or the second classification stage comprises:

providing a plurality of different specifically trained classifiers each configured to classify image data of a respective segmented dataset as normal or not-normal for a respective compartment of the respective segmented dataset, selecting one specifically trained classifier from the plurality of different specifically trained classifiers according to the at least one compartment of the segmented dataset, and classifying the image data of the segmented dataset as normal or not-normal based by applying the one specifically trained classifier to the image data.

7. The method of claim 1, further comprising:

obtaining a prior medical image dataset, the prior medical image dataset showing the body part of the patient at a different point in time as the medical image dataset, wherein at least one of the first classification stage or the second classification stage is configured to classify the medical image dataset as normal or not-normal further based on the prior medical image dataset.

8. The method of claim 7, wherein at least one of the first classification stage or the second classification stage is further configured to classify the medical image dataset as normal or not-normal based on determining a change between the medical image dataset and the prior medical image dataset.

9. The method of claim 1, further comprising:

obtaining at least one image quality parameter for the medical image dataset; and classifying the medical image dataset as not-normal based on the at least one image quality parameter.

10. The method of claim 1, further comprising:

obtaining supplementary data associated with the medical image dataset, wherein at least one of the first classification stage or the second classification stage are configured to classify the medical image dataset further based on the supplementary data.

11. The method of claim 10, further comprising:

adjusting a sensitivity of at least one of the first classification stage or the second classification stage based on the supplementary data.

12. The method of claim 10, further comprising:

checking if one or more compartments of relevance can be established based on the supplementary data;

segmenting one or more actual compartments from the medical image dataset;

checking if the one or more compartments of relevance are comprised in the one or more actual compartments; and at least one of, classifying the medical image dataset as not-normal if no compartment of relevance can be established, or classifying the medical image dataset as not-normal if at least one of the one or more compartments of relevance is not comprised in the one or more actual compartments.

13. The method of claim 10, wherein the supplementary data includes at least one of demographic data of the patient, a diagnostic task to be performed for the patient, lab data of the patient, or a medical report of the patient.

14. The method of claim 1, wherein at least one of the first classification stage or the second classification stage comprises:

calculating a confidence value for a classification result of classifying the medical image dataset as normal or not-normal, and classifying the medical image dataset as not-normal if the confidence value is below a predetermined threshold.

15. The method of claim 1, further comprising:

modifying a worklist of a user based on a classification result of classifying the medical image dataset as normal or not-normal, the worklist comprising a task for the user associated with medical image dataset.

16. The method of claim 1, further comprising:

generating a medical report based on a classification result of classifying the medical image dataset as normal or not-normal; and providing the medical report.

17. A non-transitory computer-readable medium on which program elements are stored that, when executed by a computing unit of a system for classifying a medical image dataset, cause the system to perform the method of claim 1.

18. A system for classifying a medical image dataset comprising:

an interface unit; and a computing unit, wherein the computing unit is configured to cause the system to:

receive the medical image dataset showing a body part of a patient via the interface unit, provide a first classification stage configured to classify the medical image dataset as normal or not-normal, provide a second classification stage different than the first classification stage configured to classify the medical image dataset as normal or not-normal, subject the medical image dataset to the first classification stage to classify the medical image dataset as normal or not-normal, subject the medical image dataset to the second classification stage to classify the medical image dataset as normal or not-normal if the medical image dataset is classified as normal by the first classification stage, and provide a classification result of the medical image dataset being normal or not-normal via the interface unit, wherein at least one of the first classification stage or the second classification stage includes segmenting at least one compartment from the medical image dataset to define a segmented dataset, at least one of the first classification stage or the second classification stage is configured to independently classify i) image data of the medical image dataset as normal or not-normal and ii) image data of the segmented dataset as normal or not-normal, and the medical image dataset is classified as normal if the image data of the medical image dataset is classified as normal and the image data of the segmented dataset is classified as normal.

19. A computer-implemented method for classifying a medical image dataset, the method comprising:

receiving the medical image dataset showing a body part of a patient;

providing a first classification stage configured to classify the medical image dataset as normal or not-normal;

providing a second classification stage different than the first classification stage configured to classify the medical image dataset as normal or not-normal;

subjecting the medical image dataset to the first classification stage to classify the medical image dataset as normal or not-normal;

subjecting the medical image dataset to the second classification stage to classify the medical image dataset as normal or not-normal if the medical image dataset is classified as normal by the first classification stage;

obtaining supplementary data associated with the medical image dataset, checking if one or more compartments of relevance can be established based on the supplementary data;

segmenting one or more actual compartments from the medical image dataset;

checking if the one or more compartments of relevance are comprised in the one or more actual compartments; and at least one of, classifying the medical image dataset as not-normal if no compartment of relevance can be established, or classifying the medical image dataset as not-normal if at least one of the one or more compartments of relevance is not comprised in the one or more actual compartments.

* * * * *